United States Patent

Sargent et al.

Patent Number: 5,807,868
Date of Patent: Sep. 15, 1998

[54] ISOQUINOLINE DERIVATIVES AS THERAPEUTIC AGENTS

[75] Inventors: Bruce Jeremy Sargent; David Norman Johnston; Andrew Philip Austin Crew, all of Nottingham, Great Britain

[73] Assignee: Knoll Aktiengesellschaft, Ludwigshafen, Germany

[21] Appl. No.: 564,156

[22] PCT Filed: Jun. 10, 1994

[86] PCT No.: PCT/EP94/01926

§ 371 Date: Dec. 21, 1995

§ 102(e) Date: Dec. 21, 1995

[87] PCT Pub. No.: WO95/00489

PCT Pub. Date: Jan. 5, 1995

[30] Foreign Application Priority Data

Jun. 22, 1993 [GB] United Kingdom ............ 9312807
Jun. 22, 1993 [GB] United Kingdom ............ 9312808

[51] Int. Cl.⁶ .................. A61K 31/47; C07D 217/04
[52] U.S. Cl. ............... 514/307; 546/148; 546/145; 546/146; 546/147
[58] Field of Search ................ 546/150, 148, 546/145, 146, 147; 514/307, 310

[56] References Cited

U.S. PATENT DOCUMENTS 4,292,320  9/1981  Kishimoto et al. ............ 424/258
4,370,332  1/1983  Kishimoto et al. ............ 424/258

FOREIGN PATENT DOCUMENTS

| 051 190 | 5/1982 | European Pat. Off. . |
| 058 932 | 9/1982 | European Pat. Off. . |
| 191 542 | 8/1986 | European Pat. Off. . |
| 419 247 | 3/1991 | European Pat. Off. . |
| 868 733 | 10/1939 | France . |
| 081151 | 8/1972 | Japan . |
| 3148222 | 6/1991 | Japan . |
| 995369 | 6/1965 | United Kingdom ............ 514/307 |
| 93/13073 | 7/1993 | WIPO . |

OTHER PUBLICATIONS

*Chem. Abst.,* vol. 114, No. 15, Apr. 15, 1991.
Iwasawa et al., *Jap. J. Pharmacol*, vol. 17, pp. 143–152, 1967.
*Eur. J. Pharmacol.,* vol. 184, No. 2–3, pp. 251–256, 1990.
*J. Med. Chem.,* vol. 30, pp. 1454–1458, 1987.
*Drugs of the Future,* vol. 14, No. 12, pp. 1179–1185, 1989.
*J. Med. Chem.,* vol. 31, pp. 1941–1946, 1988.
*J. Med. Chem.,* vol. 32, pp. 2050–2058, 1989.
*Eur. J. Pharmacol.,* vol. 166, pp. 481–491, 1989.
17th Cong. of Collequim Intl. Neuro–Psychopharmacologicum, Sep. 10–14, 1990, Kyoto, Japan (poster display).

Primary Examiner—Bernard Dentz
Assistant Examiner—Charanjit S. Aulakh
Attorney, Agent, or Firm—Keil & Weinkauf

[57] ABSTRACT

Tetrahydroisoquinoline compounds of formula I

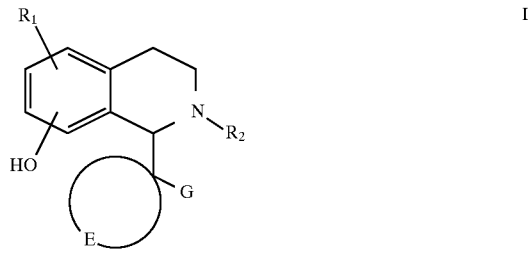

and pharmaceutically acceptable salts thereof, in which:

$R_1$ represents one or more substituents selected from H, halo, hydroxy, alkyl (optionally substituted by hydroxy), alkoxy, alkylthio, alkylsulphinyl, alkylsulphonyl, nitro, cyano, polyhaloalkyl, polyhaloalkoxy, phenyl (optionally substituted by one or more of halo, alkyl or alkoxy), or $R_1$ is optionally alkylated carbamoyl;

$R_2$ represents a saturated or unsaturated aliphatic group optionally substituted by hydroxy or alkoxy;

E represents an alkylene chain optionally substituted by one or more alkyl groups;

and G represents (a) optionally substituted saturated or unsaturated alicyclic group containing 3 to 8 carbon atoms, or (b) optionally substituted saturated or unsaturated aliphatic chain containing 1 to 12 carbon atoms, or (c) optionally substituted 5 or 6 membered heterocyclic ring containing one or more N or O atoms or $SO_n$ groups in which n is 0, 1 or 2;

and O-acylated derivatives thereof which provide lipophilic esters have utility in analgesia or in the treatment of psychoses (e.g. schizophrenia), Parkinson's disease, Lesch-Nyan syndrome, attention deficit disorder or cognitive impairment or in the relief of drug dependence or tardive dyskinesia.

19 Claims, No Drawings

ISOQUINOLINE DERIVATIVES AS THERAPEUTIC AGENTS

This application is a 371 of PCT/EP94/01926 which is now published as WO 95/00489 on Jan. 5, 1995.

The present invention relates to novel tetrahydroisoquinoline compounds, to pharmaceutical compositions containing the compounds, methods of preparing the compounds and the use of the compounds in analgesia or in the treatment of psychoses (for example schizophrenia), Parkinson's disease, Lesch-Nyan syndrome, attention deficit disorder or cognitive impairment or in the relief of drug dependence or tardive dyskinesia.

The present invention provides tetrahydroisoquinoline compounds of formula I

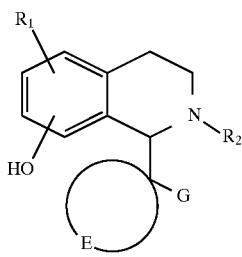

and pharmaceutically acceptable salts thereof in the form of individual enantiomers, racemates, or other mixtures of enantiomers, in which:

$R_1$ represents one or more substituents selected from H, halo, hydroxy, alkyl of 1 to 3 carbon atoms (optionally substituted by hydroxy), alkoxy of 1 to 3 carbon atoms, alkylthio of 1 to 3 carbon atoms, alkylsulphinyl of 1 to 3 carbon atoms, alkylsulphonyl of 1 to 3 carbon atoms, nitro, cyano, polyhaloalkyl of 1 to 3 carbon atoms, polyhaloalkoxy of 1 to 3 carbon atoms, phenyl (optionally substituted by one or more substituents selected from halo, alkyl of 1 to 3 carbon atoms or alkoxy of 1 to 3 carbon atoms), or $R_1$ is carbamoyl optionally substituted by one or two alkyl groups each independently of 1 to 3 carbon atoms;

$R_2$ represents a saturated or unsaturated aliphatic group containing 1 to 3 carbon atoms optionally substituted by hydroxy or alkoxy containing 1 to 3 carbon atoms;

E represents an alkylene chain containing 2 to 5 carbon atoms optionally substituted by one or more alkyl groups containing 1 to 3 carbon atoms, and G represents (a) a saturated or unsaturated alicyclic group containing 3 to 8 carbon atoms optionally substituted by one or more substitutents selected from alkyl of 1 to 3 carbon atoms, hydroxy, alkoxy of 1 to 3 carbon atoms, polyhaloalkyl of 1 to 3 carbon atoms, oxo, alkylthio of 1 to 3 carbon atoms, alkylsulphinyl of 1 to 3 carbon atoms or alkylsulphonyl of 1 to 3 carbon atoms, said alicyclic group being optionally fused to one or more further rings (for example a benz ring) to form a polycyclic group or (b) a saturated or unsaturated aliphatic chain containing 1 to 12 carbon atoms optionally substituted by one or more substituents selected from alkyl of 1 to 3 carbon atoms, hydroxy, alkoxy of 1 to 3 carbon atoms, polyhaloalkyl of 1 to 3 carbon atoms, cycloalkyl of 3 to 7 carbon atoms, oxo, alkylthio of 1 to 3 carbon atoms, alkylsulphinyl of 1 to 3 carbon atoms or alkylsulphonyl of 1 to 3 carbon atoms, or (c) a 5 or 6 membered heterocyclic ring containing one or more N or O atoms or $SO_n$ groups in which n is 0, 1 or 2, said ring being optionally substituted by one or more substituents selected from alkyl of 1 to 3 carbon atoms, alkoxy of 1 to 3 carbon atoms, hydroxy or halo and said ring being optionally fused to one or more further rings to form a polycyclic group; and O-acylated derivatives thereof.

In preferred compounds of formula I, the hydroxy group is in the 7-position. Accordingly one group of preferred compounds of the invention is represented by formula II

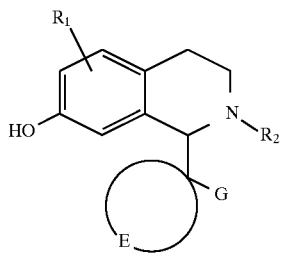

and pharmaceutically acceptable salts thereof in the form of individual enantiomers, racemates, or other mixtures of enantiomers, in which $R_1$, $R_2$, E and G are as defined above and O-acylated derivatives thereof.

A preferred group of O-acylated derivatives of compounds of formula I is represented by compounds of formula III

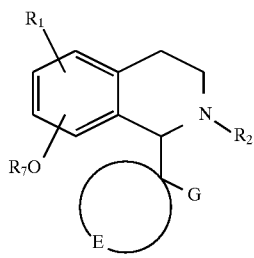

and pharmaceutically acceptable salts thereof in the form of individual enantiomers, racemates, or other mixtures of enantiomers, in which $R_1$, $R_2$, E and G are as defined above and $R_7$ represents an acyl group derived from a carboxylic acid having 6 to 20 carbon atoms, preferably 7 to 18 carbon atoms. In more preferred compounds of formula III, $R_7$ represents heptanoyl, decanoyl, dodecanoyl, hexadecanoyl or octadecanoyl. In most preferred compounds of formula III, the group $OR_7$ is in the 7-position.

In preferred compounds of formula I, II or III, $R_1$ represents H, halo, hydroxy, alkyl of 1 to 3 carbon atoms, alkoxy of 1 to 3 carbon atoms, alkylthio of 1 to 3 carbon atoms, nitro, polyfluoroalkyl of 1 to 3 carbon atoms, polyfluoroalkoxy of 1 to 3 carbon atoms or phenyl optionally substituted by fluoro, chloro, bromo, methyl or methoxy. In more preferred compounds of formula I, II or III, $R_1$ represents H, fluoro, chloro, bromo, hydroxy, methyl, methoxy, phenyl or nitro. In particularly preferred compounds of formula I, II or III, $R_1$ represents one substituent in the 6-position which is H, fluoro, chloro, bromo, hydroxy, methyl, methoxy or phenyl. In especially preferred compounds of formula I, II or III, $R_1$ represents H or methyl in the 6-position.

In preferred compounds of formula I, II or III, $R_2$ represents an alkyl group containing 1 to 3 carbon atoms optionally substituted by hydroxy or by methoxy, or $R_2$ represents an alkenyl group of 2 or 3 carbon atoms. In more preferred compounds of formula I, II or III, $R_2$ represents methyl, ethyl, 2-hydroxyethyl, 2-methoxyethyl or allyl. In particularly preferred compounds of formula I, II or III, $R_2$ represents methyl.

In preferred compounds of formula I, II or III, the group E represents —(CH$_2$)$_2$—, —(CH$_2$)$_3$—, —(CH$_2$)$_4$—, —(CH$_2$)$_5$— or —CH$_2$CMe$_2$CH$_2$—. In particularly preferred compounds of formula I, II or III, E represents —(CH$_2$)$_2$— or —(CH$_2$)$_3$—.

In preferred compounds of formula I, II or III, G represents (a) a saturated or unsaturated alicyclic group containing 5 to 7 carbon atoms optionally substituted by one or more substitutents selected from alkyl of 1 to 3 carbon atoms, hydroxy, alkoxy of 1 to 3 carbon atoms, polyfluoroalkyl of 1 to 3 carbon atoms, oxo, alkylthio of 1 to 3 carbon atoms, alkylsulphinyl of 1 to 3 carbon atoms or alkylsulphonyl of 1 to 3 carbon atoms, said alicyclic group being optionally fused to one or more further rings (for example a benz ring) to form a polycyclic group or (b) a saturated or unsaturated aliphatic chain containing 1 to 10 carbon atoms optionally substituted by one or more substituents selected from alkyl of 1 to 3 carbon atoms, hydroxy, alkoxy of 1 to 3 carbon atoms, polyfluoroalkyl of 1 to 3 carbon atoms, cycloalkyl of 3 to 7 carbon atoms, oxo, alkylthio of 1 to 3 carbon atoms, alkylsulphinyl of 1 to 3 carbon atoms or alkylsulphonyl of 1 to 3 carbon atoms, or (c) thienyl, furyl, pyrrolyl, imidazolyl, pyridyl, pyrazinyl, pyrimidinyl, triazolyl, oxazolyl, isoxazolyl, thiazolyl, isothiazolyl, triazinyl, pyridazinyl, pyranyl, furazanyl, pyrazolyl, quinolyl, isoquinolyl, quinazolinyl, quinoxalinyl, benzothienyl, benzofuranyl, indolyl, benzimidazolyl, phthalazinyl, cinnolinyl, indazolyl, indolizinyl, benzthiazolyl, benzoxazolinyl, benzodioxenyl or chromenyl and partially or fully reduced forms thereof, for example pyrrolidinyl, piperidinyl, tetrahydropyranyl, tetrahydrothiopyranyl, tetrahydrofuryl, tetrahydrothienyl, chromanyl, morpholinyl, dihydrobenzofuranyl or benzodioxanyl each of which may be optionally substituted by one or more substituents selected from halo, alkyl of 1 to 3 carbon atoms, alkoxy of 1 to 3 carbon atoms or hydroxy.

In more preferred compounds of formula I, II or III, G represents methylalkyl, cycloalkylmethyl, cycloalkenyl, 1,2,3,4-tetrahydronaphthyl, thienyl, furyl or pyridyl. In particularly preferred compounds of formula I, II or III, G represents 2-methylpropyl, cyclopentylmethyl, cyclohex-1-en-3-yl, 1,2,3,4-tetrahydronaphth-1-yl, 2-thienyl, 3-thienyl, 2-furyl or 2-pyridyl.

Specific compounds of formula I are:
7-hydroxy-2-methyl-1-[1-(2-methylpropyl)cyclobutyl]-1,2,3,4-tetrahydroisoquinoline;
1-[1-(cyclopentylmethyl)cyclopropyl]-7-hydroxy-2,6-dimethyl-1,2,3,4-tetrahydroisoquinoline;
1-[1-(cyclohex-1-en-3-yl)cyclobutyl]-7-hydroxy-2,6-dimethyl-1,2,3,4-tetrahydroisoquinoline;
7-hydroxy-2,6-dimethyl-1-[1-(1,2,3,4-tetrahydronaphth-1-yl)cyclopropyl]-1,2,3,4-tetrahydroisoquinoline;
7-hydroxy-2,6-dimethyl-1-[1-(2-thienyl)cyclopropyl]-1,2,3,4-tetrahydroisoquinoline;
7-hydroxy-2,6-dimethyl-1-[1-(3-thienyl)cyclopropyl]-1,2,3,4-tetrahydroisoquinoline;
1-[1-(2-furyl)cyclopropyl]-7-hydroxy-2,6-dimethyl-1,2,3,4-tetrahydroisoquinoline;
7-hydroxy-2-methyl-1-[1-(2-pyridyl)cyclobutyl]-1,2,3,4-tetrahydroisoquinoline;
7-hydroxy-2,6-dimethyl-1-[1-(2-pyridyl)cyclopropyl]-1,2,3,4-tetrahydroisoquinoline;
and pharmaceutically acceptable salts thereof in the form of individual enantiomers, racemates or other mixtures of enantiomers.

Specific enantiomeric forms of compounds of formula I are:

(−)-7-hydroxy-2,6-dimethyl-1-[1-(3-thienyl)cyclopropyl]-1,2,3,4-tetrahydroisoquinoline
and pharmaceutically acceptable salts thereof.

Compounds of formula I, II and III may exist as salts with pharmaceutically acceptable acids. Examples of such salts include hydrochlorides, hydrobromides, hydriodides, sulphates, nitrates, maleates, acetates, citrates, fumarates, tartrates, succinates, benzoates, palmoates, methylsulphates, dodecanoates and salts with acidic amino acids such as glutamic acid. Compounds of formula I, II and III and their salts may exist in the form of solvates (for example hydrates).

Compounds of formula III have high lipid solubility, and are therefore suitable for use in the so-called depot formulations which provide a source of active compound which is located within the body (eg by intramuscular injection). These compounds may be formulated in a pharmaceutically acceptable oil.

It will be appreciated by those skilled in the art that compounds of formula I, II and III contain a chiral centre. When a compound of formula I, II and III contains a single chiral centre it exists in two enantiomeric forms. The present invention includes the individual enantiomers and mixtures of those enantiomers. The enantiomers may be obtained by methods known to those skilled in the art. Such methods typically include resolution via formation of diastereoisomeric salts which may be separated, for example, by crystallisation; via formation of diastereoisomeric derivatives or complexes which may be separated, for example, by crystallization, gas-liquid or liquid chromatography; selective reaction of one enantiomer with an enantiomer-specific reagent, for example enzymatic esterification, oxidation or reduction; or gas-liquid or liquid chromatography in a chiral environment, for example on a chiral support such as silica with a bound chiral ligand or in the presence of a chiral solvent. It will be appreciated that where the desired enantiomer is converted into another chemical entity by one of the separation processes described above, a further step will subsequently be required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I, II or III contains more than one chiral centre it may exist in diastereoisomeric forms. The diastereoisomeric pairs may be separated by methods known to those skilled in the art, for example chromatography or crystallisation and the individual enantiomers within each pair may be separated as described above. The present invention includes each diastereoisomer of compounds of formula I or II and mixtures thereof.

Certain compounds of formula I, II or III may exist in more than one crystal form and the present invention includes each crystal form and mixtures thereof.

The present invention also provides pharmaceutical compositions comprising a therapeutically effective amount of a compound of formula I, II or III together with a pharmaceutically acceptable diluent or carrier. Such pharmaceutical formulations may be used in analgesia or in the treatment of psychoses (for example schizophrenia), Parkinson's disease, Lesch-Nyan syndrome, attention deficit disorder or cognitive impairment or in the relief of drug dependence or tardive dyskinesia.

As used hereinafter, the term "active compounds" denotes a compound of formula I, II, III. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, granules, syrups, solutions and aqueous or oil suspensions. The excipients used in the preparation of these compositions are the excipients known in the pharmacist's art. Tablets may be prepared from a mixture of the active compound with fillers, for example calcium phosphate; disintegrating agents, for example maize starch; lubricating agents, for example magnesium stearate; binders, for example micro-crystalline cellulose or polyvinylpyrrolidone and other optional ingredients known in the art to permit tableting the mixture by known methods. The tablets may, if desired, be coated using known methods and excipients which may include enteric coating using for example hydroxypropylmethylcellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by known methods and, if desired, provided with enteric coatings in a known manner. The contents of the capsule may be formulated using known methods so as to give sustained release of the active compound. The tablets and capsules may conveniently each contain 1 to 500 mg of the active compound.

Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil. The active compound may be formulated into granules with or without additional excipients. The granules may be ingested directly by the patient or they may be added to a suitable liquid carrier (for example, water) before ingestion. The granules may contain disintegrants, eg an effervescent couple formed from an acid and a carbonate or bicarbonate salt to facilitate dispersion in the liquid medium.

Compositions of the invention suitable for rectal administration are the known pharmaceutical forms for such administration, for example, suppositories with hard fat or polyethylene glycol bases.

Compositions of the invention suitable for parenteral administration are the known pharmaceutical forms for such administration, for example sterile suspensions or sterile solutions in a suitable solvent.

Compositions for topical administration may comprise a matrix in which the pharmacologically active compounds of the present invention are dispersed so that the compounds are held in contact with the skin in order to administer the compounds transdermally. Alternatively the active compounds may be dispersed in a pharmaceutically acceptable cream, gel or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or a compound of formula III as described above or (b)solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions of the present invention containing a therapeutically effective amount of a compound of formula I, II or III may be used in analgesia or to treat psychoses (for example schizophrenia), Parkinson's disease, Lesch-Nyan syndrome, attention deficit disorder or cognitive impairment or in the relief of drug dependence or tardive dyskinesia. In such treatment the amount of the compound of formula I or II which will be administered orally, rectally or parenterally per day is in the range 0.1 to 5000 mg preferably 5 to 500 mg given in a single or in divided doses at one or more times during the day.

Compounds of formula I, II or III may be administered as a method of treating Parkinson's disease either alone or in combination with a dopamine precursor such as levodopa and/or a dopa decarboxylase inhibitor such as carbidopa or benserazide.

In yet another aspect, the present invention provides the use of a compound of formula I, II or III in the manufacture of a medicament for use in analgesia or in the treatment of psychoses (for example schizophrenia), Parkinson's disease, Lesch-Nyan syndrome, attention deficit disorder or cognitive impairment or in the relief of drug dependence or tardive dyskinesia.

Processes for the preparation of compounds of formula I will now be described. These processes form a further aspect of the present invention.

Compounds of formula I may be prepared by the cleavage of compounds of formula IV

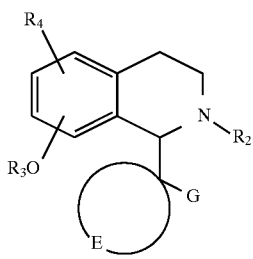

IV

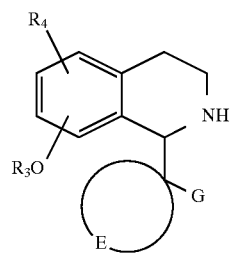

VI in which $R_3$ is an optionally substituted alkyl group (e.g. methyl or benzyl) and $R_4$ is the group $R_1$ or a group which can be converted into the group $R_1$. Demethylation may be effected by reaction with hydrobromic acid optionally in the presence of glacial acetic acid, with boron tribromide, with pyridine hydrochloride, with sodium ethanethiolate, with sodium cyanide or with trimethyliodosilane. Debenzylation may be effected by hydrolysis e.g. acid hydrolysis or by hydrogenolysis, for example using a palladium/charcoal catalyst. Compounds of formula I in which $R_1$ is hydroxy may be prepared by cleavage of compounds of formula IV in which the groups $OR_3$ and $R_4$ are the same (e.g. methoxy or benzyloxy). The cleavage of the group $R_4$ will occur simultaneously with the cleavage of the group $OR_3$.

Compounds of formula I may be prepared by the alkylation or alkenylation of compounds of formula V

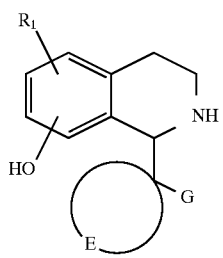

V under conditions which do not result in alkylation or alkenylation of the hydroxy group. For example, compounds of formula I in which $R_2$ is methyl may be prepared by the methylation of compounds of formula V, for example, using formaldehyde and formic acid or formaldehyde and sodium cyanoborohydride.

Compounds of formula I in which $R_1$ is other than H may be prepared by substitution reactions which will be well known to those skilled in the art. For example, compounds of formula I in which $R_1$ is nitro may be prepared by the nitration of compounds of formula I in which $R_1$ is H using nitric acid, and compounds of formula I in which $R_1$ represents one or more chloro atoms may be prepared from compounds of formula I in which $R_1$ is H by chlorination using, for example sodium hypochlorite and hydrochloric acid.

Compounds of formula II may be prepared by methods analogous to those described above for the preparation of compounds of formula I.

Compounds of formula III may be prepared from compounds of formula I by reaction with an acylating agent for example a carboxylic acid chloride of formula $R_7Cl$ or a carboxylic anhydride of formula $(R_7)_2O$.

Compounds of formula IV may be prepared by the alkylation or alkenylation of compounds of formula VI for example by reaction with an alkyl halide (e.g. methyl iodide) or an alkenyl halide (e.g. allyl iodide or bromide). Compounds of formula IV may also be prepared by reductive alkylation of compounds of formula VI, for example, by reaction with an aldehyde or ketone and a reducing agent. For example, compounds of formula IV in which $R_2$ is methyl may be prepared by the methylation of compounds of formula VI, for example, using formaldehyde and formic acid, formaldehyde and sodium dihydrogen phosphite or formaldehyde and sodium cyanoborohydride.

Compounds of formula IV in which $R_2$ is methyl may be prepared by the reaction of compounds of formula VII

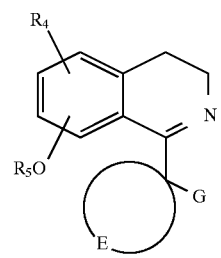

VII in which $R_5$ is the group $R_3$ under conditions which result in the reduction and methylation of the compound of formula VII, for example by the reaction of the compound of formula VII with formaldehyde and a reducing agent such as sodium cyanoborohydride or with formic acid and a reducing agent such as sodium borohydride.

Compounds of formula IV may also be prepared by the reaction of compounds of formula VIII

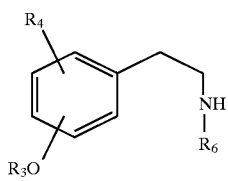

VIII in which $R_6$ is the group $R_2$ with a compound of formula IX

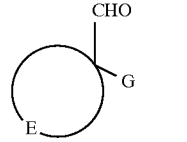

IX in the presence of an acid, for example hydrochloric acid.

Compounds of formula IV may also be prepared by the reduction of compounds of formula X

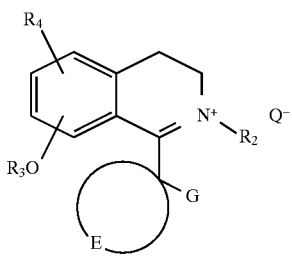

in which $Q^{\ominus}$ is a suitable anion such as iodide or methylsulphate with, for example, sodium borohydride, sodium cyanoborohydride, borane, borane-dimethylsulphide complex, lithium aluminium hydride or by catalytic hydrogenation. Chiral reducing agents such as chiral sodium triacyloxyborohydrides (for example the appropriate enantiomers of sodium tris(N-benzyloxycarbonylprolyloxy) borohydride or sodium tris[N-(2-methylpropyloxycarbonyl) prolyloxy]borohydride}, chiral dialkyloxyboranes, chiral oxazaborolidines may be used to give one of the enantiomers of the compound of formula IV. One of the enantiomers of compounds of formula IV may be prepared by catalytic hydrogenation using a chiral catalyst. A suitable catalyst is the complex formed by the reaction of a chiral phosphine [for example, 2,3-O-isopropylidene-2,3-dihydroxy-1,4-bis(diphenylphosphino)butane] with a transition metal complex [for example, chloro(1,5-cyclooctadiene)rhodium (I) dimer].

Compounds of formula V may be prepared by the cleavage of compounds of formula VI in which $R_4$ is the group $R_1$ or a group which can be converted into the group $R_1$ in a similar manner to that described above in respect of compounds of formula I.

Compounds of formula V may also be prepared by the reduction of compounds of formula VII in which $R_5$ is H, for example using reduction reactions similar to those described above for the reduction of compounds of formula X. Chiral reducing agents may be used to give one of the enantiomers of the compound of formula V in a similar manner to that described above for the reduction of compounds of formula X.

Compounds of formula VI may be prepared by the reduction of compounds of formula VII in which $R_5$ is the group $R_3$ in a similar manner to that described above for the preparation of compounds of formula IV and V.

Compounds of formula VI may be prepared by reduction of compounds of formula XI

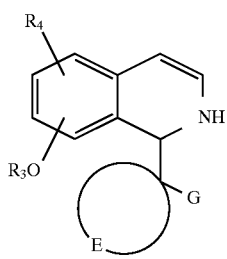

for example using catalytic hydrogenation.

Compounds of formula VI may be prepared by the reaction of a compound of formula VIII in which $R_6$ is H with a compound of formula IX in the presence of an acid for example hydrochloric acid.

Compounds of formula VII may be prepared by the cyclisation of compounds of formula XII

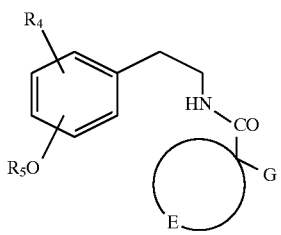

in which $R_5$ is H or $R_3$. The cyclisation may be effected in the presence of a condensing agent such as phosphorus oxychloride, phosphorus pentoxide, phosphorus pentachloride, polyphosphoric ester, polyphosphoric acid, zinc chloride, hydrochloric acid, thionyl chloride or sulphuric acid.

Compounds of formula VII may be prepared by the reaction of a compound of formula XIII

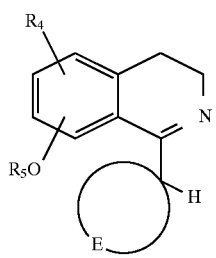

with a base such as lithium diisopropylamide and a compound of formula X—G in which X is a leaving group such as tosyloxy or halo.

Compounds of formula VII in which the group G is a hydroxy-substituted group of formula XIV

wherein $R_8$ and $R_9$, which may be the same or different, represent an optionally substituted saturated or unsaturated aliphatic chain or together with the carbon atom to which they are attached form an optionally substituted saturated or unsaturated alicyclic group, may be prepared by the reaction of a compound of formula XIII with a base such as lithium diisopropylamide and a compound of formula XV

Compounds of formula VII in which the group G is a hydroxy-substituted heterocyclic group of formula XVI

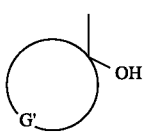

wherein G' is an alkylene chain interrupted by one or more O atoms or by one or more groups of formula $SO_n$, may be prepared by the reaction of a compound of formula XIII with a base such as lithium diisopropylamide and a compound of formula XVII

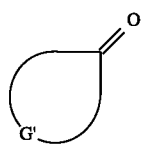
XVII

Compounds of formula IX may be prepared by reduction of cycloalkanecarbonitriles of formula XVIII

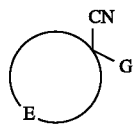
XVIII by di-t-butylaluminium hydride or di-isobutyl aluminium hydride or reduction of cycloalkane carbonyl chlorides of formula XIX

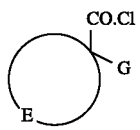
XIX with lithium tri-t-butoxyaluminohydride.

Compounds of formula X may be prepared by the reaction of a compound of formula VII in which $R_5$ is the group $R_3$ with an alkylating agent of formula $R_2Q$, for example methyl iodide or dimethylsulphate.

Compounds of formula XI may be prepared by the cyclisation of compounds of formula XX

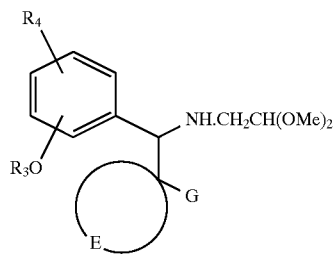
XX

The cyclisation may be effected in the presence of an acid such as sulphuric acid.

Compounds of formula XII may be prepared by the reaction of a phenethylamine of formula XXI

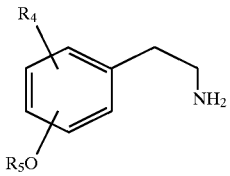
XXI in which $R_5$ is H or $R_3$ with a cycloalkanecarbonyl chloride of formula XIX for example in the presence of an organic base such as triethylamine. Compounds of formula XII may also be prepared by the condensation of a phenethylamine of formula XXI with a cycloalkane carboxylic acid of formula XXII

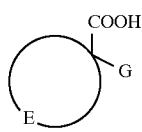
XXII or an ester thereof, for example by fusion or by the action of a condensing agent such as 1,1-carbonyldiimidazole, or 1,3-dicyclohexylcarbodiimide.

Compounds of formula XIII may be prepared by cyclisation of compounds of formula XXIII

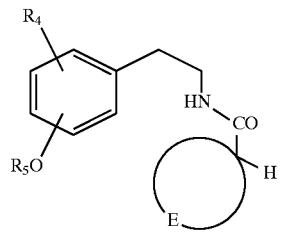
XXIII under conditions similar to those described above for the cyclisation of compounds of formula XII.

Cycloalkanecarbonitriles of formula XVIII may be prepared by the reaction of a carbonitrile of formula XXIV $$G—CH_2—CN \qquad XXIV$$

with a di-substituted compound of formula XXV $$Z—E—Z' \qquad XXV$$

in which Z and Z', which may be the same or different, are leaving groups such as halo e.g. chloro or bromo in the presence of a base such as sodium hydride or potassium hydroxide.

Cycloalkanecarbonitriles of formula XVIII may also be prepared by reaction of a carbonitrile of formula XXVI

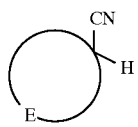
XXVI with a base such as lithium diisopropylamide and a compound of formula X—G in which X is a leaving group (for example halo).

Cycloalkanecarbonyl chlorides of formula XIX may be prepared from cycloalkane carboxylic acids of formula XXII by methods which are well known in the art, for example, by reaction with thionyl chloride.

Compounds of formula XX may be prepared by the reaction of a compound of formula XXVII

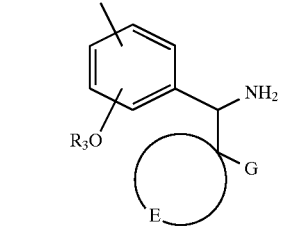
XXVII with a haloacetaldehyde dimethylacetal for example chloroacetaldehyde dimethylacetal.

Cycloalkane carboxylic acids of formula XXII may be prepared by the hydrolysis (e.g. basic hydrolysis) of cycloalkanecarbonitriles of formula XVIII or by the reaction of hydrogen peroxide with cycloalkanecarbonitriles of formula XVIII in the presence of a base followed by reaction with nitrous acid to give the required carboxylic acid.

Compounds of formula XXIII may be prepared by the reaction of a phenylethylamine of formula XXI with a cycloalkane carbonyl chloride of formula XXVIII

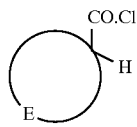

XXVIII

Compounds of formula XXVII may be prepared by the reaction of a compound of formula XXIX

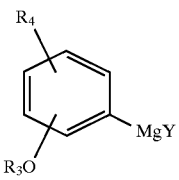

XXIX in which Y is halo (eg chloro or bromo) with a cycloalkanecarbonitrile of formula XVIII followed by reduction with, for example, sodium borohydride.

Compounds of formula XXIX may be prepared by the reaction of magnesium with a compound of formula XXX

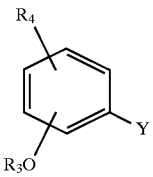

XXX in which Y is halo (eg bromo or chloro).

The ability of compounds of formula I or formula II to interact with dopamine receptors has been demonstrated by the following tests which determine the ability of the compounds to inhibit tritiated ligand binding to dopamine receptors in vitro and in particular to the D1 and D2 dopamine receptors.

Striatal samples from the brains of male Charles River CD rats weighing between 140–250 g were homogenised in ice-cold 50 mM Tris-HCl buffer (pH 7.4 when measured at 25° C. for D1 binding assays and pH 7.7 when measured at 25° C. for D2 binding assays) and centrifuged for 10 minutes (at 21,000 g when used for D1 binding assay and 40,000 g when used for D2 binding assays). The pellet was resuspended in the same buffer, again centrifuged and the final pellet stored at −80° C. Before each test the pellet was resuspended in 50 mM Tris-HCl buffer containing 120 mM NaCl, 5 mM KCl, 2 mM $CaCl_2$ and 1 mM $MgCl_2$ at pH 7.4 for the D1 binding assays and at pH 7.7 with the addition of 6 mM ascorbic acid for the D2 binding assays. Aliquots of this suspension were then added to tubes containing the ligand and either the compound under test or buffer. For the D1 binding assays the ligand was tritiated SCH 23390 and the mixture was incubated at 37° C. for 30 minutes before the incubation was terminated by rapid filtration. For the D2 binding assays the ligand was tritiated (S)-sulpiride and the mixture was incubated at 4° C. for 40 minutes before the incubation was terminated by rapid filtration. Non-specific binding was determined experimentally by the addition of saturating concentrations of chlorpromazine or spiroperidol for D1 and D2 receptors respectively.

The filters were washed with ice-cold Tris-HCl buffer and dried. The filters were punched out into vials containing scintillation fluid and were left for about 20 hours before being counted by scintillation spectrophotometry. Competition binding curves were produced over a range of concentrations of the compound under test and the inhibition coefficient Ki was derived from the data by use of the non-linear curve fitting computer programe EBDA (Biosoft).

The $K_i$ values obtained in the above tests for D1 and D2 binding for each of the final products of the Examples hereinafter are given in Table I below which also shows the ratio between these two values to two significant figures.

TABLE I

| Example | $K_i$ for D1 binding (nM) | $K_i$ for D2 binding (nM) | $\dfrac{K_i \text{ for D2}}{K_i \text{ for D1}}$ |
|---|---|---|---|
| 1 | 370 | 25000 | 68 |
| 2 | 7.9 | 2300 | 290 |
| 3 | 77 | 9500 | 120 |
| 4 | 6.7 | 190 | 28 |
| 5 | 32 | 3000 | 94 |
| 6 | 2.1 | 4900 | 2300 |
| 7 | 4.2 | 8500 | 2000 |
| 8 | 5.9 | 1300 | 220 |
| 9 | 40 | 8900 | 220 |
| 10 | 160 | 7000 | 44 |
| 11 | 140 | 1100 | 79 |

The invention is illustrated by the following Examples which are given by way of example only. In these Examples all temperatures are given in degrees Celsius. The final products of each of these Examples were characterised by one or more of the following procedures: elemental analyses, nuclear magnetic resonance spectroscopy and infra red spectroscopy.

EXAMPLE 1

Cyclobutanecarbonyl chloride (5.5 g) was added to a solution of 2-(4-methoxyphenyl)ethylamine (7 g) and triethylamine (6.5 ml) in ether (300 ml) at ambient temperature. The mixture was stirred overnight, poured onto water and acidified with 2M hydrochloric acid, then the mixture was extracted with ethyl acetate (3×100 ml). The combined extracts were washed with brine, dried and the solvents removed in vacuo to give a residue. This was washed with petroleum ether and dried in vacuo to give N-[2-(4-methoxyphenyl)ethyl]cyclobutanecarboxamide as a solid (9.54 g), mp 118°–20° C.

A portion of the solid (9 g), in dry acetonitrile (170 ml) containing phosphorus oxychloride (23.7 ml) was heated under reflux for 43 hours. The cooled mixture was then poured onto dilute ammonia solution and the mixture extracted with ethyl acetate (3×150 ml). The ethyl acetate solution was then extracted with dilute hydrochloric acid (3×100 ml). The aqueous acid extracts were neutralized by addition of aqueous ammonia solution and extracted with ethyl acetate. The organic extracts were washed with brine, dried and concentrated to give an oil which was distilled at 190° C./0.2 mbar to give 1-cyclobutyl-7-methoxy-3,4-dihydroisoquinoline as a colourless solid (4 g), mp 44°–46° C.

n-Butyllithium (2.83 ml, 1.8M in hexanes) was added dropwise to a solution of diisopropylamine (0.71 ml) in dry tetrahydrofuran (5 ml) at ambient temperature. After 15 minutes the solution was cooled to −23° C. and treated slowly with a solution of 1-cyclobutyl-7-methoxy-3,4-dihydroisoquinoline (1 g) in tetrahydrofuran (11 ml). The dark green solution was stirred for 30 minutes, further cooled to −78° C. and treated with 1-bromo-2-methylpropane (5.1 ml). After 1 hour at −78° C. the mixture was allowed to warm to ambient temperature, then heated under reflux for 1 hour. The mixture was poured onto water, acidified, and washed with ether. The aqueous phase was then basified by addition of aqueous sodium hydroxide solution and extracted with ethyl acetate. The solvent was removed in vacuo to yield an orange gum which was purified by flash chromatography over silica gel using a 1:4 mixture of ethyl acetate and light petroleum ether as eluant to give 7-methoxy-1-[1-(2-methylpropyl)cyclobutyl]-3,4-dihydroisoquinoline as an oil (0.85 g).

A mixture of the oil (0.98 g, prepared in a similar manner to that described above), tetrahydrofuran (15 ml) and sodium borohydride (1 g) was cooled to 0° C. and treated dropwise very slowly with formic acid (10.3 ml). The mixture was allowed to warm to ambient temperature, and stirred for 2 days. The mixture was poured onto water, basified by addition of aqueous sodium hydroxide solution and extracted with ether. The extracts were dried and the solvent removed in vacuo to give a gum which very slowly solidified. This was dissolved in ether and treated with an ethereal solution of racemic dibenzoyltartaric acid and the precipitate filtered off and dried in vacuo. The salt was recrystallised from propan-2-ol to give 7-methoxy-2-methyl-1-[1-(2-methylpropyl)cyclobutyl]-1,2,3,4-tetrahydroisoquinoline dibenzoyltartrate (0.8 g), mp 135°–136° C.

The above salt was neutralised and the free base (0.3 g) was heated under gentle reflux for 3 hours in a mixture of 48% hydrobromic acid (12 ml) and acetic acid (12 ml). The solvent was removed in vacuo and the residue dried by azeotropic distillation with propan-2-ol. The residue was suspended in propan-2-ol and collected by filtration. The filter cake was washed with further propan-2-ol then dried in vacuo to yield pure 7-hydroxy-2-methyl-1-[1-(2-methylpropyl)cyclobutyl]-1,2,3,4-tetrahydroisoquinoline hydrobromide (0.3 g), mp 241°–244° C. (dec).

EXAMPLE 2

A solution of butyllithium in hexane (2.5M; 80 ml) was added to a solution of diisopropylamine (27.8 ml) and 1,3-dimethyl-3,4,5,6-tetrahydro-2(1H)-pyrimidinone (28.6 ml) in tetrahydrofuran (188 ml) stirring at 0° C. Stirring was continued for 0.5 hours then the mixture was cooled to −78° C. and cyclopropanecarbonitrile (13.4 g) was added. After stirring at −78° C. for a further 1 hour cyclopentylmethylbromide (37.6 g) was added slowly, then the mixture allowed to warm to ambient temperature and stirred for a further 18 hours. The mixture was poured onto water (1l) then extracted with ethyl acetate (4×150 ml). The combined extracts were washed with brine then dried over magnesium sulphate and then the solvent was removed in vacuo. Solid material was removed by filtration and the residual oil triturated with ether, solid material again being removed by filtration. The residual oil was then purified by distillation under reduced pressure giving 1-(cyclopentylmethyl)cyclopropanecarbonitrile (8.9 g) as an oil, bp 50° C./1 mbar.

The product from the previous reaction (8.9 g), powdered potassium hydroxide (85%; 6.6 g) and 1,2-ethanediol (65 ml) were heated together under reflux for 50 hours. The mixture was poured into water (200 ml) then washed with ether. The aqueous phase was acidified with concentrated hydrochloric acid, then extracted with ether (5×50 ml). The combined extracts were dried over magnesium sulphate and the solvent was removed in vacuo to give 1-(cyclopentylmethyl)cyclopropanecarboxylic acid (8.2 g) as a tan solid, mp 42°–45° C.

A solution of 1,1-carbonyldiimidazole (8.05 g) in tetrahydrofuran (125 ml) was added dropwise to a solution of the product from the previous reaction (8.2 g) in tetrahydrofuran (125 ml) stirring at 0° C. The mixture was stirred at ambient temperature for 18 hours then a solution of 2-(4-methoxy-3-methylphenyl)ethylamine hydrochloride (8.9 g) and triethylamine (6.27 ml) in tetrahydrofuran (200 ml) was added. The mixture was stirred at ambient temperature for 18 hours, then poured onto water (500 ml) and basified with aqueous ammonia solution. The mixture was then extracted with ethyl acetate (5×100 ml), the combined extracts were washed with dilute hydrochloric acid, then brine, then dried over magnesium sulphate. The solvent was removed in vacuo to leave N-[2-(4-methoxy-3-methylphenyl)ethyl]-1-(cyclopentylmethyl)cyclopropanecarboxamide (10.6 g) as a gum.

A mixture of the product from the previous reaction (10.55 g), phosphorus oxychloride (21.3 ml) and acetonitrile (170 ml) was heated under reflux for 4.5 hours then cooled and poured onto ice-water (200 ml). The mixture was basified with aqueous ammonia solution then extracted with ethyl acetate (4×60 ml). The combined extracts were washed with brine then dried over magnesium sulphate and the solvent removed in vacuo to give a viscous gum which was partially purified by flash chromatography on silica using a 2:1 mixture of petroleum ether (bp 60°–80° C.) and ethyl acetate as eluant to give crude 1-[1-(cyclopentylmethyl)cyclopropyl]-7-methoxy-6-methyl-3,4-dihydroisoquinoline (5.0 g) which was used without further purification.

Sodium cyanoborohydride (2.13 g) was added in one portion to an ice-cooled solution of the crude product from the previous reaction (5.0 g) in a mixture of methanol (25 ml) and acetic acid (50 ml). After stirring at ambient temperature for 18 hours the mixture was poured into dilute aqueous sodium hydroxide solution (150 ml) and extracted with ethyl acetate (4×50 ml). The combined extracts were washed with brine then dried over magnesium sulphate and the solvent removed in vacuo to leave a gum which was purified by flash chromatography on silica using a 5:1 mixture of petroleum ether (bp 60°–80° C.) and triethylamine as eluant to give 1-[1-(cyclopentylmethyl)cyclopropyl]-7-methoxy-6-methyl-1,2,3,4-tetrahydroisoquinoline (2.65 g) as a gum.

Sodium cyanoborohydride (2.37 g) was added to a solution of the product from the previous reaction (2.65 g) and aqueous formaldehyde solution (37%; 4.65 ml) in methanol (80 ml) and the mixture stirred for 5 hours. The mixture was poured into dilute aqueous ammonia solution (150 ml) then extracted with ethyl acetate (4×60 ml). The combined extracts were dried over magnesium sulphate and the solvent removed in vacuo. The residue was dissolved in ether (150 ml) and hydrogen chloride gas passed through the solution; the resulting precipitate was filtered and dried to give 1-[1-(cyclopentylmethyl)cyclopropyl]-7-methoxy-2,6-dimethyl-1,2,3,4-tetrahydroisoquinoline hydrochloride (2.1 g), mp 166°–169° C.

The product from the previous reaction (2.0 g) and tetrabutylphosphonium bromide (0.19 g) were heated together in hydrobromic acid (48%; 15 ml) at 95° C. for 24 hours then poured onto water (100 ml) and the mixture basified with aqueous ammonia solution. The mixture was extracted with ethyl acetate (4×40 ml) and the combined extracts were washed with brine then dried over magnesium sulphate. The solvent was removed in vacuo to give a residual red oil which still appeared to contain starting material. The residue was then dissolved in a mixture of acetic acid (20 ml) and hydrobromic acid (48%; 20 ml) and the mixture heated at 95° C. for 18 hours then poured into water (150 ml) and washed with ether. The aqueous phase was basified with aqueous ammonia solution then extracted with ethyl acetate (4×50 ml) and the combined extracts washed with brine then dried over magnesium sulphate. The solvent was removed in vacuo to leave a brown oil which was dissolved in ether (150 ml) then treated with an excess of a saturated solution of oxalic acid in ether. The resultant precipitate was recrystallised from acetonitrile but the product remained impure. The free base was regenerated by partition between dilute aqueous ammonia solution (50 ml) and ethyl acetate (50 ml). The organic phase was separated and the aqueous phase extracted with ethyl acetate (3×20 ml). The combined organics were washed with brine then dried over magnesium sulphate. The solvent was removed in vacuo and the residue triturated with ether to give a solid which recrystallised from acetonitrile to give 1-[1-(cyclopentylmethyl)cyclopropyl]-7-hydroxy-2,6-dimethyl-1,2,3,4-tetrahydroisoquinoline (0.15 g), mp 136°–138° C.

EXAMPLE 3

Cyclobutanecarbonyl chloride (7 g) was added dropwise to a solution of 2-(4-methoxy-3-methylphenyl)ethylamine (11.36 g) and triethylamine (13 ml) in tetrahydrofuran (150 ml) and the resulting suspension stirred for 16 hours. The mixture was poured into water (150 ml), acidified with dilute hydrochloric acid and extracted with ethyl acetate (4×50 ml). The combined organic extracts were washed with brine then dried over magnesium sulphate and the solvent removed in vacuo. The residue was washed with petroleum ether (bp 40°–60° C.) to give crude N-[2-(4-methoxy-3-methylphenyl)ethyl]cyclobutanecarboxamide (12 g). A sample recrystallised from acetonitrile had mp 103°–104° C.

A solution of the the crude product from the reaction above (12 g) and phosphorus oxychloride (28 ml) in acetonitrile (240 ml) was heated under gentle reflux for 2.75 hours, cooled, then poured into dilute aqueous ammonia solution (700 ml). The mixture was extracted with ethyl acetate (4×80 ml). The combined extracts were washed with brine then dried over magnesium sulphate and the solvent removed in vacuo. The residual gum was partitioned between ether (150 ml) and hydrochloric acid (3M; 150 ml) and the organic phase further extracted with hydrochloric acid (3M; 3×60 ml). The combined aqueous acid solutions were washed with ether, basified with aqueous ammonia solution, then extracted with ethyl acetate (6×80 ml). The combined extracts were washed with brine then dried over magnesium sulphate and the solvent removed in vacuo to give 1-cyclobutyl-7-methoxy-6-methyl-3,4-dihydroisoquinoline (8.4 g) as a gum which was used without further purification.

A solution of t-butyllithium in pentane (1.7M; 25.8 ml) was added dropwise to a solution of the crude product from the reaction above (8.4 g) in tetrahydrofuran (130 ml) at −78° C. under nitrogen, and the mixture stirred at this temperature for 1 hour. 3-Bromocyclohexene (11.76 g) was added dropwise and the solution was stirred at −78° C. for 1 hour, then allowed to warm to ambient temperature.

The solution was poured into dilute hydrochloric acid (300 ml) and washed with ether. The aqueous phase was basified with aqueous ammonia solution then extracted with ethyl acetate (4×60 ml). The combined extracts were washed with brine then dried over magnesium sulphate and the solvent removed in vacuo to give an orange oil. This was dissolved in ether (250 ml) and a solution of (±) dibenzoyltartaric acid (0.3M; 25 ml) was added. After stirring for 20 minutes the precipitate was filtered and discarded. The filtrate was neutralised with concentrated aqueous ammonia solution and extracted with ether (4×50 ml). The solvent was removed in vacuo to give an oil which was purified by flash chromatography on silica using a 5:1 mixture of petroleum ether (bp 60°–80° C.) and triethylamine as eluant to give 1-[1-(cyclohex-1-en-3-yl)cyclobutyl]-7-methoxy-6-methyl-3,4-dihydroisoquinoline (5.9 g) as a gum which slowly solidified, mp 70°–73° C.

Sodium cyanoborohydride (0.6 g) was added to a solution of the product of the previous reaction (1.5 g) in acetic acid (16 ml) and methanol (8 ml) and the solution stirred for 16 hours. Aqueous sodium hydroxide solution (20%; 150 ml) was added, then the mixture was extracted with ethyl acetate (4×50 ml). The combined organic extracts were washed with aqueous sodium hydroxide solution (0.1M), water, then brine, then dried over magnesium sulphate. The solvent was removed in vacuo to leave 1-[1-(cyclohex-1-en-3-yl) cyclobutyl]-7-methoxy-6-methyl-1,2,3,4-tetrahydroisoquinoline (1.47 g) as a colourless gum which was used without further purification.

Aqueous formaldehyde solution (37% w/w; 1.8 ml) was added to a solution of the product from the previous reaction (1.47 g) in acetonitrile (60 ml) giving a colourless precipitate. Sodium cyanoborohydride (0.47 g) was added and the mixture stirred for 20 minutes before neutralisation with acetic acid. After 50 minutes aqueous sodium hydroxide solution (10%; 200 ml) was added and the mixture was extracted with ethyl acetate (4×50 ml). The combined extracts were washed with brine, then dried over magnesium sulphate and the solvent removed in vacuo. The residual solid was recrystallised from acetonitrile (50 ml) to give 1-[1-(cyclohex-1-en-3-yl)cyclobutyl]-7-methoxy- 2,6-dimethyl-1,2,3,4-tetrahydroisoquinoline (1.1 g) as a colourless solid, mp 124°–125° C.

Sodium hydride (60% oil dispersion; 0.51 g) was added in portions to an ice-cooled solution of ethanethiol (0.94 ml) in dry dimethylformamide (7.6 ml) and the mixture stirred whilst being allowed to warm to ambient temperature during 20 minutes. A suspension of the product from the previous reaction (0.9 g) in dry dimethylformamide (25 ml) was added slowly, then the mixture was heated at 140° C. for 6 hours. After standing at ambient temperature for 2.5 days the mixture was poured onto iced water (150 ml), washed with petroleum ether (bp 60°–80° C.), then the pH was adjusted to 6 with hydrochloric acid (2M) and the mixture again washed with petroleum ether. The mixture was basified with aqueous ammonia solution and extracted with dichloromethane (3×40 ml) followed by ethyl acetate (4×60 ml). The ethyl acetate extracts were combined and dried over magnesium sulphate and the solvent was removed in vacuo. The residue was dissolved in ether and treated with an excess of a solution of oxalic acid in ether. The resulting precipitate was recrystallised from industrial methylated spirit to give 1-[1-(cyclohex-1-en-3-yl)cyclobutyl]-7-hydroxy-2,6-dimethyl-1,2,3,4-tetrahydroisoquinoline oxalate (0.28 g) as a mixture of diastereoisomers, mp 194°–196° C.

EXAMPLE 4

Cyclopropanecarbonitrile (17.14 g) was added dropwise to a mixture of lithium diisopropylamide solution (2M in a mixture of heptane, tetrahydrofuran and ethylbenzene; 128 ml), 1,3-dimethyl-3,4,5,6-tetrahydro-2(1H)-pyrimidinone (30 ml) and tetrahydrofuran (240 ml) stirring at −78° C. under nitrogen. Stirring was continued for 1 hour at this temperature then a solution of 1-chlorotetralin (48.4 g) in tetrahydrofuran (50 ml) was added slowly and after a further hour the solution was allowed to warm to ambient temperature, then was heated under gentle reflux for 2 hours. The solvent was removed in vacuo and the residue acidified with concentrated hydrochloric acid then extracted with ethyl acetate (4×100 ml). The combined extracts were dried over magnesium sulphate and the solvent removed in vacuo to leave a semi-solid which was filtered and washed with acetonitrile, then recrystallised from acetone to give 1-(1,2,3,4-tetrahydronaphth-1-yl)cyclopropanecarbonitrile (8.3 g), mp 91°–93° C.

A mixture of the product of the previous reaction (8.3 g), powdered potassium hydroxide (85%; 4.66 g) and 1,2-ethanediol (50 ml) was heated under gentle reflux under nitrogen for 7 days. The mixture was diluted with water (200 ml) and washed well with ether. The aqueous phase was then acidified with concentrated hydrochloric acid and extracted with ethyl acetate (5×150 ml). The extracts were dried and the solvent removed in vacuo. The resultant solid was recrystallised from acetonitrile to give 1-(1,2,3,4-tetrahydronaphth-1-yl)cyclopropanecarboxylic acid (2.25 g), mp 140°–142° C. The ethereal washings were shown to contain unreacted starting nitrile which was heated with potassium hydroxide (85%; 1.8 g) in 1,2-ethanediol (20 ml) for 2.5 days. Work up as above followed by recrystallisation from acetonitrile gave a further crop of the desired product (2.45 g).

A solution of 1,1-carbonyldiimidazole (3.2 g) in tetrahydrofuran (50 ml) was added slowly to a solution of the product from the previous reaction (4.3 g) in tetrahydrofuran (50 ml) and the mixture stirred for 18 hours. 2-(4-Methoxy-3-methylphenyl)ethylamine hydrochloride (4.0 g) then triethylamine (2.8 ml) were added and the mixture stirred for 18 hours. As the reaction had not gone to completion a solution of further starting amine (3.09 g) and triethylamine (2.1 ml) in tetrahydrofuran (20 ml) was added and stirring continued for three days. As the reaction remained incomplete, dilute aqueous sodium hydroxide solution (200 ml) was added and stirring continued for 18 hours. The organic layer was separated and the aqueous layer extracted with ethyl acetate (4×150 ml). The combined organics were washed with brine then dried over magnesium sulphate and the solvent removed in vacuo. The residue was washed well with petroleum ether (bp 60°–80° C.) to give crude N-[2-(4-methoxy-3-methylphenyl)ethyl]-1-(1,2,3,4-tetrahydronaphth-1-yl)cyclopropanecarboxamide (7.0 g) as a brown gum which was used without further purification.

A mixture of the crude product from the previous reaction (7.0 g), phosphorus oxychloride (11 ml) and acetonitrile (90 ml) was heated under reflux for 3 hours. The cooled solution was then poured carefully into dilute aqueous ammonia solution (200 ml) and extracted with ethyl acetate (4×150 ml). The combined extracts were washed with brine then dried over magnesium sulphate, the solvent removed in vacuo and the residue purified by flash chromatography on silica using a 2:1 mixture of petroleum ether (bp 60°–80° C.) and ethyl acetate as eluant to give 7-methoxy-6-methyl-1-[1-(1,2,3,4-tetrahydronaphth-1-yl)-cyclopropyl]-3,4-dihydroisoquinoline as a dark gum (1.5 g).

Sodium cyanoborohydride (0.53 g) was added in one portion to a solution of the product of the previous reaction (1.46 g) in a mixture of methanol (7 ml) and acetic acid (14 ml) and the mixture stirred for 18 hours. The mixture was poured into water (150 ml), then basified with concentrated aqueous ammonia solution and extracted with ethyl acetate (4×60 ml). The combined extracts were washed with brine then dried over magnesium sulphate and the solvent removed in vacuo to give 7-methoxy-6-methyl-1-[1-(1,2,3,4-tetrahydronaphth-1-yl)cyclopropyl]-1,2,3,4-tetrahydroisoquinoline as a yellow oil (1.58 g) which was used without further purification.

Sodium cyanoborohydride (0.47 g) was added to a stirring solution of the product of the previous reaction (1.5 g) and aqueous formaldehyde solution (37%; 1.8 ml) in acetonitrile (60 ml). After 20 minutes acetic acid (2 ml) was added and stirring continued for one hour, then the mixture was poured into dilute aqueous ammonia solution (150 ml) and extracted with ethyl acetate (4×100 ml). The combined extracts were dried and the solvent removed in vacuo. The residue was purified by flash chromatography on silica using a 2:1 mixture of petroleum ether (bp 60°–80° C.) and ethyl acetate as eluant to give 7-methoxy-2,6-dimethyl-1-[1-(1,2,3,4-tetrahydronaphth-1-yl)cyclopropyl]-1,2,3,4-tetrahydroisoquinoline (1.2 g) as a colourless oil.

The product from the previous reaction (1.2 g), in a mixture of acetic acid (40 ml) and hydrobromic acid (48%; 40 ml), was heated at 95° C. for 3 days. The cooled mixture was poured into water (150 ml) then washed with ether. The aqueous phase was basified with concentrated aqueous ammonia solution then extracted with ethyl acetate (5×100 ml). The combined extracts were washed with brine then dried over magnesium sulphate and the solvent removed in vacuo to give a dark brown gum. Purification by flash chromatography on silica using a 4:1 mixture of petroleum ether (bp 60°–80° C.) and ethyl acetate as eluant gave a gum which was dissolved in ether (150 ml) then treated with hydrogen chloride and the resultant precipitate filtered and dried to give 7-hydroxy-2,6-dimethyl-1-[1-(1,2,3,4-tetrahydronaphth-1-yl)cyclopropyl]-1,2,3,4-tetrahydroisoquinoline 1.05 hydrochloride 0.7 hydrate (0.74 g), mp 160°–163° C.

EXAMPLE 5

2-Thiopheneacetonitrile (50 g) was added dropwise to a vigorously stirred mixture of 50% w/w aqueous sodium hydroxide solution (190 ml), 1,2-dibromoethane (150 g) and benzyltriethylammonium chloride (10 g). The stirred mixture was heated at 75° C. for 3 hours then cooled and acidified with 5M hydrochloric acid, the mixture was filtered and the filtrate extracted with ethyl acetate (4×100 ml). The combined extracts were washed with brine, dried and the solvent removed in vacuo. The resulting black gum was decolourised with charcoal in boiling methanol to give a brown gum (53.6 g). The gum was washed with light petroleum to afford 1-(2-thienyl)cyclopropanecarbonitrile as a solid (42 g), mp 118°–122° C.

The solid (42 g) in a suspension of potassium hydroxide (31.2 g) in ethylene glycol (300 ml), was stirred and heated at gentle reflux for 16 hours. The cooled mixture was poured onto water (1000 ml). This solution was washed well with ether, then acidified and extracted with ethyl acetate (4×150 ml). The combined organic extracts were washed with water, then brine and dried. The solvent was removed in vacuo to give 1-(2-thienyl)cyclopropanecarboxylic acid (37.6 g), mp 116°–118° C.

A mixture of 2-(4-methoxy-3-methylphenyl)ethylamine (16 g), triethylamine (1.74 ml), 1,3-dicyclohexylcarbodiimide (8.75 g), 1-(2-thienyl)

cyclopropanecarboxylic acid (7 g) and 1-hydroxybenzotriazole (5.6 g) in tetrahydrofuran (95 ml) was stirred for 16 hours. The mixture was poured into water, basified with aqueous ammonia solution and filtered. The filtrate was extracted with ethyl acetate (3×50 ml) and the combined extracts washed with 1M hydrochloric acid and brine then dried and the solvent removed in vacuo. The resulting gum was treated with acetonitrile and insoluble matter filtered off. Evaporation of the filtrate gave crude N-[2-(4-methoxy-3-methylphenyl)ethyl]-1-(2-thienyl) cyclopropanecarboxamide as a solid (10.7 g), which was used without further purification.

A portion of this carboxamide (3.5 g) in a solution of acetonitrile (52 ml) and phosphorus oxychloride (6.5 ml) was heated under reflux for 2.5 hours. The cooled reaction mixture was then poured onto dilute ammonia solution and the product extracted with ethyl acetate. The combined extracts were washed with brine then dried and the solvents removed in vacuo to give a dark gum. This was purified by flash chromatography on silica gel using a 5:1 mixture of light petroleum ether and triethylamine as eluant to give crude 7-methoxy-6-methyl-1-[1-(2-thienyl)cyclopropyl]-3,4-dihydroisoquinoline (4.4 g).

A solution of this dihydroisoquinoline (1.85 g) in glacial acetic acid (20 ml) and methanol (10 ml) was cooled in ice and treated portionwise with sodium cyanoborohydride (0.77 g). The reaction mixture was stirred for 16 hours then poured onto water, basified with concentrated sodium hydroxide solution and extracted with ethyl acetate (3×50 ml). The combined extracts were washed with 1M sodium hydroxide solution, water and brine, then dried and the solvent removed in vacuo to give 7-methoxy- 6-methyl-1-[1-(2-thienyl)cyclopropyl]-1,2,3,4-tetrahydroisoquinoline as a colourless gum.

The gum (2 g, prepared in a similar manner to that described above) in acetonitrile (80 ml) and 37% w/w aqueous formaldehyde solution (2.6 ml) was treated with sodium cyanoborohydride (0.67 g). After 15 minutes the mixture was neutralised with acetic acid then stirred for a further 45 minutes. The mixture was basified by addition of 2M sodium hydroxide solution and the product extracted with ethyl acetate (4×50 ml). The combined organic extracts were washed with 0.1M aqueous sodium hydroxide solution, water and brine, dried and concentrated to yield a gum. This was purified by flash chromatography on silica gel using a 1:49 mixture of methanol and dichloromethane as eluant to give crude 7-methoxy-2,6-dimethyl-1-[1-(2-thienyl)cyclopropyl]-1,2,3,4-tetrahydroisoquinoline as a solid (1.1 g).

A solution of the 2,6-dimethyltetrahydroisoquinoline (2.07 g, prepared in a similar manner to that described above) in dichloromethane (10 ml) was cooled to −76° C. and treated dropwise with a 1M solution of boron tribromide in dichloromethane (6.6 ml). After stirring at ambient temperature for 2 days the mixture was poured onto methanol (150 ml) and concentrated to near dryness. Methanol was added and evaporated a further three times then finally propan-2-ol was added and all solvent was removed in vacuo. The residue was recrystallised from industrial methylated spirit to give 7-hydroxy-2,6-dimethyl-1-[1-(2-thienyl) cyclopropyl]-1,2,3,4-tetrahydroisoquinoline hydrobromide (1.1 g), mp 245°–246° C.

EXAMPLE 6

A solution of thiophene-3-acetonitrile (30 g) and 1-bromo-2-chloroethane (40.8 ml) in dimethyl sulphoxide (120 ml) was added slowly dropwise to a well stirred suspension of sodium hydride (60% dispersion in mineral oil; 38.8 g) in dimethyl sulphoxide (800 ml) at 30°–35° C. The solution was stirred at ambient temperature for 21 hours then water (100 ml) was carefully added followed by hydrochloric acid (2M; 100 ml). The mixture was extracted with ether (6×80 ml) and the combined extracts washed with water (2×100 ml) then brine and then dried over magnesium sulphate. The solvent was removed in vacuo and the residue washed with petroleum ether (bp 60°–80° C.) before distillation under reduced pressure which gave 1-(3-thienyl) cyclopropanecarbonitrile as an oil (26.3 g), bp 82°–86° C./2 mbar.

The product from the previous reaction (26.0 g) and powdered potassium hydroxide (85%; 19.0 g) were heated together in 1,2-ethanediol (190 ml) at just below reflux temperature for 3 days. The cooled reaction mixture was poured onto water (600 ml) and washed with ether. The aqueous phase was acidified with concentrated hydrochloric acid and extracted with ethyl acetate (6×200 ml). The combined extracts were washed with brine then dried over magnesium sulphate and the solvent removed in vacuo. The residue was triturated with ether to give 1-(3-thienyl) cyclopropanecarboxylic acid (20 g) as a cream solid, mp 132°–133° C.

A solution of N,N'-dicyclohexylcarbodiimide (24.76 g) in tetrahydrofuran (30 ml) was added to a solution of the product of the previous reaction (20 g), 2-(4-methoxy-3-methylphenyl)ethylamine hydrochloride (22.2 g) and 4-(dimethylamino)pyridine (13.4 g) in tetrahydrofuran (150 ml) and the mixture stirred for 18 hours. The mixture was diluted with water, acidified with concentrated hydrochloric acid then extracted with ethyl acetate (4×100 ml). The combined extracts were washed with dilute aqueous sodium hydroxide solution and brine then dried over magnesium sulphate. The solvent was removed in vacuo to give crude N-[2-(4-methoxy-3-methylphenyl)ethyl]-1-(3-thienyl) cyclopropanecarboxamide (38.4 g) as a pale yellow gum which was used without further purification.

A mixture of the crude product from the previous reaction (38.4 g), phosphorus oxychloride (60 ml) and acetonitrile (500 ml) was heated under reflux for 3.5 hours. The cooled solution was poured into water (1 l) and carefully basified with concentrated aqueous ammonia solution. The mixture was extracted with ether (5×100 ml). The first of these extracts on standing deposited crystals of the desired product (3.8 g) which were filtered and dried. The other extracts were combined and dried over magnesium sulphate and the solvent removed in vacuo. The residue was recrystallised from acetonitrile to give a second crop of product (8.8 g). The mother liquors were evaporated and the residue purified by flash column chromatography on silica using a 2:1 mixture of ethyl acetate and petroleum ether (bp 60°–80° C.) as eluant, followed by recrystallisation from acetonitrile to give a third crop of product (2.0 g). The three crops were combined to give 7-methoxy-6-methyl-1-[1-(3-thienyl) cyclopropyl]-3,4-dihydroisoquinoline (14.6 g), mp 116°–118° C.

Sodium cyanoborohydride (0.84 g) was added in one portion to a solution of the product from the previous reaction (2.0 g) in a mixture of methanol (10 ml) and acetic acid (20 ml) and the mixture stirred for 3 hours before pouring into water (200 ml) and basifying with concentrated aqueous ammonia solution. The mixture was extracted with ethyl acetate (4×60 ml), the combined extracts washed with brine then dried over magnesium sulphate, and the solvent removed in vacuo to give crude 7-methoxy-6-methyl-1-[1-

(3-thienyl)cyclopropyl]-1,2,3,4-tetrahydroisoquinoline (2.1 g) as a colourless gum.

Sodium cyanoborohydride (0.67 g) was added to a solution of the crude product from the previous reaction (2 g) in a mixture of aqueous formaldehyde solution (37%; 2.6 ml) and acetonitrile (80 ml). After stirring for 15 minutes the mixture was acidified with acetic acid and stirring continued for 1 hour before pouring into water (200 ml), basifying with concentrated aqueous ammonia solution and extraction with ethyl acetate (4×60 ml). The combined extracts were washed with brine, dried over magnesium sulphate and the solvent removed in vacuo. The residue was recrystallised from acetonitrile to give 7-methoxy-2,6-dimethyl-1-[1-(3-thienyl)cyclopropyl]-1,2,3,4-tetrahydroisoquinoline (1.7 g) as a colourless solid, mp 103°–105° C.

A mixture of the product from the previous reaction (1.7 g), hydrobromic acid (48%; 60 ml) and acetic acid (60 ml) was stirred and heated at 150° C. for 3 hours. The mixture was poured into water (300 ml), basified with concentrated aqueous ammonia, then extracted with ethyl acetate (4×150 ml). The combined extracts were washed with brine then dried over magnesium sulphate and the solvent removed in vacuo to give 7-hydroxy-2,6-dimethyl-1-[1-(3-thienyl) cyclopropyl]-1,2,3,4-tetrahydroisoquinoline (1.3 g) as a gum. A further sample of this compound (1.8 g) was prepared as above on 1.47×scale. The combined material was then separated into its enantiomers by preparative scale chiral high performance liquid chromatography using a 95:5 mixture of hexane and 2-propanol as eluant at 30 ml/min. and UV detection at 254 nm. The individual (−) enantiomer, $[\alpha]_D = -19.4°$ (C=0.95, $CH_2Cl_2$), was treated with an excess of a saturated solution of oxalic acid in ether and the resultant salt recrystallised from industrial methylated spirit giving (−)-7-hydroxy-2,6-dimethyl-1-[1-(3-thienyl) cyclopropyl]-1,2,3,4-tetrahydroisoquinoline oxalate (140 mg), mp 222° C., $[\alpha]_D = -118.6°$ (c=1, MeOH).

EXAMPLE 7

A solution of 7-methoxy-6-methyl-1-[1-(3-thienyl) cyclopropyl]-3,4-dihydroisoquinoline (2.0 g, prepared in a similar manner to that described in Example 6) in dichloromethane (87 ml) was added slowly to an ice-cooled stirred mixture of sodium tris[(S)-N-(tert-butoxycarbonyl) prolyloxy]borohydride (11.4 g) in dichloromethane (70 ml). After standing at about 4° C. for 2 days a further portion of the reducing agent (2.0 g) was added and the mixture stirred at ambient temperature for 3 hours, then saturated aqueous oxalic acid solution (150 ml) was added. This mixture was stirred for 1 hour then basified with concentrated aqueous ammonia solution and extracted with dichloromethane (4×100 ml). The combined extracts were washed with water (100 ml) then brine (100 ml) then dried over magnesium sulphate and the solvent removed in vacuo to give a pale orange gum. The gum was dissolved in ether (150 ml) and treated with a solution of oxalic acid in ether (0.43M; 20 ml) and the resulting precipitate filtered then recrystallised from ethanol to give a single enantiomer of 7-methoxy-6-methyl-1-[1-(3-thienyl)cyclopropyl]-1,2,3,4-tetrahydroisoquinoline oxalate (1.2 g) which was used without further characterisation.

Sodium cyanoborohydride (0.28 g) was added to a stirred suspension of the product from the previous reaction (1.1 g) in a mixture of acetonitrile (35 ml) and aqueous formaldehyde solution (37%; 1.1 ml). After 3 hours the mixture was poured into water (150 ml), basified with concentrated aqueous ammonia solution, then extracted with ethyl acetate (5×50 ml). The combined extracts were washed with water (100 ml) then brine (100 ml) and dried over magnesium sulphate. The solvent was removed in vacuo and the residual solid recrystallised from acetonitrile to give (−)-7-methoxy-2,6-dimethyl-1-[1-(3-thienyl)cyclopropyl]-1,2,3,4-tetrahydroisoquinoline (0.75 g) as colourless crystals, $[\alpha]_D = -44.8°$ (c=0.5, $CH_2Cl_2$).

A mixture of the product from the previous reaction (0.65 g), hydrobromic aced (48%; 9 ml) and acetic acid (9 ml) was heated at 150° C. under nitrogen for 3 hours. The mixture was partitioned between ether (50 ml) and water (100 ml), the aqueous Layer adjusted to pH 8 by slow addition of concentrated aqueous ammonia solution then the ether layer was separated and the aqueous further extracted with ether (2×100 ml) then ethyl acetate (3×100 ml). The combined extracts were washed with brine then dried over magnesium sulphate and the solvents removed in vacuo to give a pale yellow gum which was dissolved in ether (150 ml) and treated with a solution of oxalic acid in ether (0.43M; 7 ml) and the resulting gelatinous precipitate collected by filtration. This material was recrystallised from industrial methylated spirit to give in two crops (−)-7-hydroxy-2,6-dimethyl-1-[1-(3-thienyl)cyclopropyl]-1,2,3,4-tetrahydroisoquinoline oxalate (0.53 g) identical to that prepared in example 6.

The oxalate was partitioned between ether (50 ml) and water (100 ml) and the aqueous layer adjusted to pH 8 by slow addition of concentrated aqueous ammonia solution. The ether layer was separated and the aqueous further extracted with ether (2×100 ml) then ethyl acetate (3×100 ml). The combined extracts were washed with brine then dried over magnesium sulphate and the solvents removed in vacuo to give a pale yellow gum. The gum was triturated with dichloromethane (2 ml) to give the corresponding free base as a pale yellow solid (0.42 g) mp 155°–157° C., $[\alpha]_D -19.4°$ (c=0.95, $CH_2Cl_2$). The free base was dissolved in ether (120 ml) and treated with hydrogen chloride gas for 1 minute. The precipitate was collected by filtration and dried in vacuo to give (−)-7-hydroxy-2,6-dimethyl-1-[1-(3-thienyl)cyclopropyl]-1,2,3,4-tetrahydroisoquinoline hydrochloride 0.8 hydrate (0.41 g), mp 149°–152° C. (dec.), $[\alpha]_D -124.3°$ (c=0.6, MeOH).

EXAMPLE 8

The demethylation procedure described in Example 6 was repeated on 1.2×scale, the solvents being removed from the cooled reaction mixture in vacuo. The residue was recrystallised from acetone to give (±)-7-hydroxy-2,6-dimethyl-1-[1-(3-thienyl)cyclopropyl]-1,2,3,4-tetrahydroisoquinoline hydrobromide (1.1 g) as an off white solid, mp 230° C. (dec.)

EXAMPLE 9

A solution of furan-2-acetonitrile (28.4 g) and 1-bromo-2-chloroethane (33.1 ml) in dimethyl sulphoxide (50 ml) was added slowly to a stirred suspension of sodium hydride (60% dispersion in mineral oil ; 31.85 g) in dry dimethyl sulphoxide (300 ml) keeping the internal temperature just below 35° C. by occasional cooling. After stirring for 18 hours at ambient temperature the mixture was diluted with water (500 ml) and extracted with ether (1×200 then 2×100 ml). The combined extracts were dried over potassium carbonate and evaporated to an oil which was distilled at reduced pressure to give 1-(2-furyl) cyclopropanecarbonitrile (28.0 g) as a colourless oil, bp 54° C./0.55 mbar.

A mixture of the product of the previous reaction (28.0 g), potassium hydroxide (25.0 g), methanol (20 ml) and water (250 ml) was heated under reflux for 90 minutes. The methanol was distilled off under reduced pressure and the aqueous solution washed with ether then acidified with ice-cold hydrochloric acid (2M). The precipitate was filtered, washed well with water and air dried to give 1-(2-furyl)cyclopropanecarboxylic acid (27.5 g) as a colourless solid, mp 113°–114° C.

A solution of the product from the previous reaction (7.6 g) in dry tetrahydrofuran (125 ml) was added to a solution of 1,1-carbonyldiimidazole (8.1 g) in dry tetrahydrofuran (125 ml) and the mixture allowed to stand for 18 hours with the exclusion of moisture. 2-(4-Methoxy-3-methylphenyl)ethylamine hydrochloride (9.8 g) was added followed by triethylamine (14.4 ml) and the mixture stirred for 18 hours with the exclusion of moisture. Water (200 ml) was added and the mixture made strongly basic with aqueous sodium hydroxide solution (2M). The mixture was extracted with ether (3×80 ml) and the combined extracts dried over potassium carbonate then the solvent removed in vacuo to give crude 1-(2-furyl)-N-[2-(4-methoxy-3-methylphenyl)ethyl]cyclopropanecarboxamide (13.4 g) as an oil.

A solution of the crude product from the previous reaction (8.4 g) in ethyl polyphosphate (40 g) was swirled at 95° C. under nitrogen for 40 minutes. The mixture was poured onto a mixture of ice (200 g) and aqueous ammonia solution (60 ml) then extracted with ether (3×70 ml). The solvent was evaporated from the combined extracts and the residue was purified by flash column chromatography on silica using a 17:2:1 mixture of petroleum ether (bp 40°–60° C.), ether and triethylamine as eluant to give 1-[1-(2-furyl)cyclopropyl]-7-methoxy-6-methyl-3,4-dihydroisoquinoline (1.36 g) as a colourless crystalline solid, mp 98°–100° C.

Sodium borohydride (2.0 g) was added in small portions to a stirring solution of the product from the previous reaction (1.2 g) in industrial methylated spirit (100 ml). The mixture was allowed to stand for 18 hours then heated at reflux for one hour. The solvent was removed in vacuo, water (100 ml) was added to the residue which was then extracted with ether (2×50 ml). The combined extracts were dried over potassium carbonate and the solvent removed in vacuo to give 1-[1-(2-furyl)cyclopropyl]-7-methoxy-6-methyl-1,2,3,4-tetrahydroisoquinoline (1.2 g) as an oil.

Sodium cyanoborohydride (0.7 g) was added to a stirring solution of the product of the previous reaction (1.2 g) in a mixture of methanol (60 ml) and aqueous formaldehyde solution (37%; 3.0 ml). After stirring for 18 hours the methanol was removed in vacuo below 40° C. and the aqueous residue basified with a mixture of ice (50 g) and aqueous ammonia solution (20 ml) then extracted with ether (3×40 ml). The combined extracts were dried over potassium carbonate and the solvent removed in vacuo to give 1-[1-(2-furyl)cyclopropyl]-7-methoxy-2,6-dimethyl-1,2,3,4-tetrahydroisoquinoline (1.3 g) as a gum.

Sodium ethanethiolate (2.0 g) was added to a stirred solution of the product of the previous reaction (1.3 g) in dimethylformamide (25 ml) then the mixture was heated at 180° C. for 1.5 hours. The cooled mixture was diluted with water (200 ml), acidified with ice-cold hydrochloric acid (5M) then washed with ether (3×80 ml). The aqueous layer was basified with aqueous ammonia solution and extracted with ether (3×80 ml). The combined extracts were dried over sodium sulphate and the solvent removed in vacuo to leave a brown oil which was purified by flash chromatography on silica using a 50:45:5 mixture of petroleum ether (bp 40°–60° C.), ether and triethylamine as eluant. The product was treated with a solution of maleic acid in ether. The solvent was decanted from the resulting gum which was then triturated with boiling ethyl acetate. The resulting colourless solid was dried giving 1-[1-(2-furyl)cyclopropyl]-7-hydroxy-2,6-dimethyl-1,2,3,4-tetrahydroisoquinoline maleate (0.77 g), mp 155° C.

EXAMPLE 10

Cyclobutanecarbonyl chloride (5.5 g) was added to a solution of 2-(4-methoxyphenyl)ethylamine (7 g) and triethylamine (6.5 ml) in ether (300 ml), at ambient temperature. The mixture was stirred overnight, poured onto water and acidified with 2M hydrochloric acid, then the product was extracted with ethyl acetate (3×100 ml). The combined extracts were washed with brine, dried and the solvents removed in vacuo to give a residue. This was washed with light petroleum and dried in vacuo to give N-[2-(4-methoxyphenyl)ethyl]cyclobutanecarboxamide (9.54 g), mp 118°–120° C.

A solution of this amide (9 g) in dry acetonitrile (170 ml) containing phosphorus oxychloride (23.7 ml) was heated under reflux for 43 hours. The cooled mixture was then poured onto dilute ammonia solution and this mixture extracted with ethyl acetate (3×150 ml). The ethyl acetate solution was then extracted with dilute hydrochloric acid (3×100 ml). The aqueous acid extracts were basified by addition of aqueous ammonia solution and the mixture extracted with ethyl acetate. The organic extracts were washed with brine and concentrated to give an oil which was distilled at 190° C./0.2 mbar to give 1-cyclobutyl-7-methoxy-3,4-dihydroisoquinoline as a colourless solid (4 g), mp 44°–46° C.

n-Butyllithium (7.3 ml, 2.09M in hexanes) was added dropwise at ambient temperature to a solution of diisopropylamine (2.12 ml) in dry tetrahydrofuran (14 ml). After 15 minutes, the solution was cooled to −23° C. and a solution of 1-cyclobutyl-7-methoxy-3,4-dihydroisoquinoline (3 g) in tetrahydrofuran (34 ml) was added. After 30 minutes the mixture was cooled to −78° C., treated with 2-chloropyridine (1.56 ml), stirred for 1 hour then warmed to ambient temperature. The mixture was heated under reflux for 5 minutes, stirred for 16 hours at ambient temperature, then heated under reflux for 30 minutes. The reaction mixture was poured onto water and extracted with ethyl acetate. The extracts were dried and concentrated and the residual orange oil heated at 90° C. at 13.3 mbar to remove excess 2-chloropyridine. The residue was purified by flash chromatography over silica gel using a 5:1 mixture of light petroleum and triethylamine as eluant to give 7-methoxy-1-[1-(2-pyridyl)cyclobutyl]-3,4-dihydroisoquinoline as a solid (0.58 g).

A mixture of the dihydroisoquinoline (1.06 g, prepared in a similar manner to that described above), glacial acetic acid (12 ml) and methanol (6 ml) was treated at 0°–10° C. with sodium cyanoborohydride (0.47 g) and stirred for 16 hours then poured onto aqueous sodium hydroxide. The product was extracted with ethyl acetate (3×100 ml), and the combined extracts washed with dilute aqueous ammonia solution and brine. The organic layer was then dried, the solvent removed in vacuo and the residual oil dissolved in ether and treated with ethereal oxalic acid solution. The resulting solid was collected by filtration to yield 7-methoxy-1-[1-(2-pyridyl)cyclobutyl]-1,2,3,4-tetrahydroisoquinoline oxalate (1.06 g), mp 135°–138° C.

A portion of the above solid (0.95 g) in methanol (32 ml) containing 37% w/w aqueous formaldehyde solution (1.9 ml) was treated with sodium cyanoborohydride (1 g) and the reaction stirred for 16 hours. The mixture was then concentrated and the residue basified with aqueous sodium hydroxide solution. The mixture was extracted with ethyl acetate (3×100 ml) and the combined extracts washed with dilute ammonia solution and brine. The extracts were dried and the solvent removed in vacuo to give an oil which was purified by flash chromatography over silica gel using a 5:1 mixture of light petroleum and triethylamine as eluant to give 7-methoxy-2-methyl-1-[1-(2-pyridyl)cyclobutyl]-1,2,3,4-tetrahydroisoquinoline as an oil (0.52 g).

A solution of the 2-methyltetrahydroisoquinoline (0.52 g) in 48% aqueous hydrobromic acid (15 ml) and glacial acetic acid (15 ml) was heated under reflux for 4 hours. Solvents were removed in vacuo and the residue dried by azeotropic distillation with propan-2-ol. The residue was crystallised from propan-2-ol to give the hydrobromide salt as a solid. This was collected by filtration, neutralised and converted (by treatment with an ethereal solution of oxalic acid) into 7-hydroxy-2-methyl-1-[1-(2-pyridyl)cyclobutyl]-1,2,3,4-tetrahydroisoquinoline oxalate, mp 95°–97° C. (dec).

EXAMPLE 11

50% Aqueous sodium hydroxide solution (100 ml) was added to a stirred mixture of 2-(2-pyridyl)acetonitrile (25 g), 1-bromo-2-chloroethane (26.5 ml), benzyltriethylammonium chloride (1 g) and toluene (100 ml) at 25° C., then the mixture was heated at 70°–75° C. for 2 hours. The solution was cooled to ambient temperature, charcoal was added, and the solution was filtered (Celite). The product was extracted into ether (2×100 ml), the combined organic extracts were dried over potassium carbonate and the solvent was removed in vacuo to yield a red/orange solid (28 g). The solid was distilled at 150° C./10, mbar to yield 1-(2-pyridyl)cyclopropanecarbonitrile (26.1 g) as a solid.

1-(2-Pyridyl)cyclopropanecarbonitrile (26 g) was heated under reflux for 2 hours with 10% aqueous potassium hydroxide solution (140 ml). After cooling, the solution was washed with toluene (2×100 ml) and acidified by the addition of a mixture of concentrated sulphuric acid (5.7 ml) and water (50 ml). The solvent was removed in vacuo and the residue dried by azeotropic distillation with methanol. The residue was suspended in methanol (100 ml), the solution was filtered, and the solvent was removed in vacuo to yield 1-(2-pyridyl)cyclopropanecarboxylic acid (28 g) as an oil.

Trimethylorthoacetate (38.0 g) was added to a solution of 1-(2-pyridyl)cyclopropanecarboxylic acid (17.2 g) in toluene (200 ml) under nitrogen. The mixture was stirred under reflux for 24 hours, then cooled to ambient temperature and washed with aqueous sodium hydroxide solution (2M; 2×100 ml) and water (2×100 ml). The mixture was then dried over sodium sulphate and the solvent removed in vacuo to yield a brown oil (12.8 g). The product was purified by flash column chromatography over silica gel using a 5:1 mixture of triethylamine and petroleum ether (bp 40°–60° C.) as eluant to yield methyl 1-(2-pyridyl)cyclopropanecarboxylate as a yellow/green oil (11.5 g).

Methyl 1-(2-pyridyl)cyclopropanecarboxylate (9.4 g) and 2-(4-methoxy-3-methylphenyl)ethylamine (8.8 g; prepared by neutralisation of the hydrochloride (14.6 g)) were stirred at 95° C. under nitrogen for 16 hours. The mixture was stirred at 110° C. under nitrogen for 24 hours, then dissolved in dichloromethane (100 ml) and washed with aqueous hydrochloric acid (2M; 2×100 ml). The mixture was dried over magnesium sulphate and the solvent removed in vacuo to yield crude N-(2-(4-methoxy-3-methylphenyl)ethyl 1-(2-pyridyl)cyclopropanecarboxamide (2.1 g). The aqueous layer was basified with aqueous sodium hydroxide solution, then extracted with dichloromethane (2×10 ml). The organic layer was dried over magnesium sulphate, combined with the original carboxamide (2.1 g) and concentrated in vacuo. The product was purified by flash column chromatography over silica gel using a 1:1 mixture of ethyl acetate and petroleum ether (bp 40°–60° C.) to yield N-(2-(4-methoxy-3-methylphenyl)ethyl 1-(2-pyridyl)cyclo-propane carboxamide (4.4 g), mp 65°–66° C.

A solution of the amide (1.0 g, prepared in a similar manner to that described above) in polyphosphate ester (50% w/w in $CHCl_3$; 10 g) was heated at 95° C. with stirring under nitrogen for 16 hours. The mixture was cooled, quenched with ice water (100 ml), washed with ether (100 ml), basified with aqueous ammonia solution (25% v/v) and extracted with ethyl acetate (3×100 ml). The combined organic layers were dried over sodium sulphate and the solvent removed in vacuo to yield 7-methoxy-6-methyl-1-[1-( 2-pyridyl)-cyclopropyl]-3,4-dihydroisoquinoline (0.9 g).

A solution of this dihydroisoquinoline (3.1 g, prepared in a similar manner to that described above) in methanol (18 ml) and glacial acetic acid (36 ml) was stirred at 0°–10° C. and treated with sodium cyanoborohydride (1.38 g) and the resulting solution was stirred at ambient temperature for 14 hours. The solution was basified by the addition of aqueous sodium hydroxide solution (2N), then extracted with ethyl acetate (2×100 ml). The combined organic layers were washed with aqueous ammonia solution (25% v/v; 100 ml) and brine (100 ml), then dried over sodium sulphate and the solvent removed in vacuo to yield a brown oil (2.5 g).

The brown oil (2.5 g) was dissolved in ether and ethereal oxalic acid was added. A white gum precipitated and was isolated by decanting then purified by repeated trituration with ether and a 3:1 mixture of ether and ethyl acetate. The resulting white powder was basified with aqueous sodium carbonate solution and extracted with ethyl acetate. The organic layer was washed with water, dried over sodium sulphate and the solvent removed in vacuo to yield 7-methoxy-6-methyl-1-[1-(2-pyridyl)cyclopropyl]-1,2,3,4-tetrahydroisoquinoline as a brown oil (0.7 g).

A solution of tetrahydroisoquinoline (0.7 g, prepared as described above) in methanol (30 ml) and formaldehyde (37–40% w/w; 1.9 ml) was stirred and treated with sodium cyanoborohydride (1 g). The solution was stirred for 5 minutes, then glacial acetic acid was added until the mixture had pH 6. The mixture was stirred for a further 40 minutes, then concentrated in vacuo and basified using aqueous sodium hydroxide solution (2N). The product was extracted with ethyl acetate (2×100 ml) and the combined organic extracts were washed with aqueous ammonia solution (25% v/v; 100 ml) and brine (100 ml), dried over sodium sulphate and the solvent removed in vacuo to yield a brown oil. The oil was dissolved in ether and ethereal oxalic acid was added. The resulting precipitate was triturated with ether to yield 7-methoxy-2,6-dimethyl-1-[1-(2-pyridyl)cyclopropyl]-1,2,3,4-tetra-hydroisoquinoline (0.7 g).

A solution of 7-methoxy-2,6-dimethyl-1-[1-(2-pyridyl)cyclopropyl]-1,2,3,4-tetrahydroisoquinoline (0.7 g) in 48% hydrobromic acid (10 ml) and glacial acetic acid (10 ml) was heated under reflux under nitrogen for 5 hours. The mixture was cooled to ambient temperature, and concentrated in vacuo. Water (50 ml) was added and the solution basified with aqueous sodium hydroxide solution (2N) until the solution had pH 8. The product was extracted with ether (100 ml) and ethyl acetate (200 ml), and the combined organic fractions were washed with water (100 ml). The organic layer was dried over sodium sulphate and the solvents removed in vacuo to yield a brown solid which was triturated with ether to yield 7-hydroxy-2,6-dimethyl-1-[1-(2-pyridyl)cyclopropyl]-1,2,3,4-tetrahydroisoquinoline (0.3 g) as a solid, mp 218° C. (Dec).

EXAMPLE 12

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose of part of a unit dose of active compound.

b) Tablets

Tablets are prepared from the following ingredients.

|  | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

e) Injections

Injections are prepared from the following ingredients.

|  | % w/v |
|---|---|
| Active compound | 0.4 |
| Sodium acid phosphate BP | 0.8 |
| Sodium phosphate BP | 0.02 |
| Disodium edetate BP | 0.05 |
| Sodium chloride BP | 0.1 |
| Water for injections BP | to 100 |

The active compound is dissolved in water for injections, with the aid of the pH adjusting and/or buffering agents. The other agents are added then the water is added to make the correct volume. The injection solution would then be filtered to remove particulate matter and sterilised by suitable means (eg heating in an autoclave or aseptic filtration). The solution is packed into unit dose ampoules or syringes.

f) Depot injections

Injections are prepared from the following ingredients.

|  | % w/v |
|---|---|
| Active compound | 2.5 |
| Sesame oil BP | to 100 |

The active compound is dissolved in the sesame oil then sterilised by filtration and packed aseptically into unit dose ampoules or syringes.

What is claimed is:

1. Tetrahydroisoquinoline compounds of formula I

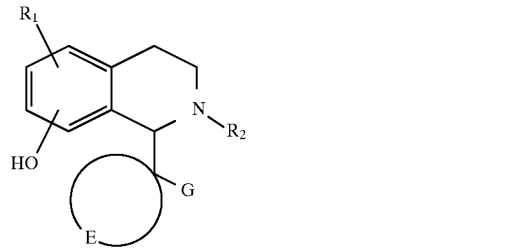

and pharmaceutically acceptable salts thereof in the form of individual enantiomers, racemates, or other mixtures of enantiomers, in which:

$R_1$ represents one or more substituents selected from H, halo, hydroxy, alkyl of 1 to 3 carbon atoms (optionally substituted by hydroxy), alkoxy of 1 to 3 carbon atoms, alkylthio of 1 to 3 carbon atoms, alkylsulphinyl of 1 to 3 carbon atoms, alkylsulphonyl of 1 to 3 carbon atoms, nitro, cyano, polyhaloalkyl of 1 to 3 carbon atoms, polyhaloalkoxy of 1 to 3 carbon atoms, phenyl (optionally substituted by one or more substituents selected from halo, alkyl of 1 to 3 carbon atoms or alkoxy of 1 to 3 carbon atoms), or $R_1$ is carbamoyl optionally substituted by one or two alkyl groups each independently of 1 to 3 carbon atoms;

$R_2$ represents a saturated or unsaturated aliphatic group containing 1 to 3 carbon atoms optionally substituted by hydroxy or alkoxy containing 1 or 3 carbon atoms;

E represents an alkylene chain containing 2 to 5 carbon atoms optionally substituted by one or more alkyl groups containing 1 to 3 carbon atoms, and G represents a 5 to 6 membered heterocyclic ring having one or more N or O atoms or $SO_n$ groups in which n is 0, 1 or 2, said ring being optionally substituted by one or more substituents selected from alkyl of 1 to 3 carbon atoms, alkoxy of 1 to 3 carbon atoms, hydroxy or halo and said ring being optionally fused to one or more further rings to form a polycyclic group; and O-acylated derivatives thereof.

2. Tetrahydroisoquinoline compounds of formula I as claimed in claim 1 in which $R_1$ represents H, halo, hydroxy, alkyl of 1 to 3 carbon atoms, alkoxy of 1 to 3 carbon atoms, alkylthio of 1 to 3 carbon atoms, nitro, polyfluoroalkyl of 1 to 3 carbon atoms, polyfluoroalkoxy of 1 to 3 carbon atoms or phenyl optionally substituted by fluoro, chloro, bromo, methyl or methoxy.

3. Tetrahydroisoquinoline compounds of formula I as claimed in claim 1 in which $R_1$ represents H, fluoro, chloro, bromo, hydroxy, methyl, methoxy, phenyl or nitro.

4. Tetrahydroisoquinoline compounds of formula I as claimed in claim 1 in which $R_2$ represents an alkyl group containing 1 to 3 carbon atoms optionally substituted by hydroxy or by methoxy, or $R_2$ represents an alkenyl group of 2 or 3 carbon atoms.

5. Tetrahydroisoquinoline compounds of formula I as claimed in claim 1 in which $R_2$ represents methyl, ethyl, 2-hydroxyethyl, 2-methoxyethyl or allyl.

6. Tetrahydroisoquinoline compounds of formula I as claimed in claim 1 in which E represents —(CH$_2$)$_2$—, —(CH$_2$)$_3$—, —(CH$_2$)$_4$—, —(CH$_2$)$_5$— or —CH$_2$CMe$_2$CH$_2$—.

7. Tetrahydroisoquinoline compounds of formula I as claimed in claim 1 in which G represents (a) a saturated or unsaturated alicyclic group containing 5 to 7 carbon atoms optionally substituted by one or more substituents selected from alkyl of 1 to 3 carbon atoms, hydroxy, alkoxy of 1 to 3 carbon atoms, polyfluoroalkyl of 1 to 3 carbon atoms, oxo, alkylthio of 1 to 3 carbon atoms, alkylsulphinyl of 1 to 3 carbon atoms or alkylsulphonyl of 1 to 3 carbon atoms, said alicyclic group being optionally fused to one or more further rings to form a polycyclic group or (b) a saturated or unsaturated aliphatic chain containing 1 to 10 carbon atoms optionally substituted by one or more substituents selected from alkyl of 1 to 3 carbon atoms, hydroxy, alkoxy of 1 to 3 carbon atoms, polyfluoroalkyl of 1 to 3 carbon atoms, cycloalkyl of 3 to 7 carbon atoms, oxo, alkylthio of 1 to 3 carbon atoms, alkylsulphinyl of 1 to 3 carbon atoms or alkylsulphonyl of 1 to 3 carbon atoms, or (c) thienyl, furyl, pyrrolyl, imidazolyl, pyridyl, pyrazinyl, pyrimidinyl, triazolyl, oxazolyl, isoxazolyl, thiazolyl, isothiazolyl, triazinyl, pyridazinyl, pyranyl, furazanyl, pyrazolyl, quinolyl, isoquinolyl, quinazolinyl, quinoxalinyl, benzothienyl, benzofuranyl, indolyl, benzimidazolyl, phthalazinyl, cinnolinyl, indazolyl, indolizinyl, benzthiazolyl, benzoxazolinyl, benzodioxenyl or chromenyl and partially or fully reduced forms thereof, for example pyrrolidinyl, piperidinyl, tetrahydropyranyl, tetrahydrothiopyranyl, tetrahydrofuryl, tetrahydrothienyl, chromanyl, morpholinyl, dihydrobenzofuranyl or benzodioxanyl each of which may be optionally substituted by one or more substituents selected from halo, alkyl of 1 to 3 carbon atoms, alkoxy of 1 to 3 carbon atoms or hydroxy.

8. Tetrahydroisoquinoline compounds of formula I as claimed in claim 1 in which G represents methylalkyl, cycloalkylmethyl, cycloalkenyl, 1,2,3,4-tetrahydronaphthyl, thienyl, furyl or pyridyl.

9. Tetrahydroisoquinoline compounds of formula I as claimed in claim 1 which are:
7-hydroxy-2-methyl-1-[1-(2-methylpropyl)cyclobutyl]-1,2,3,4-tetrahydroisoquinoline;
1-[1-(cyclopentylmethyl)cyclopropyl]-7-hydroxy-2,6-dimethyl-1,2,3,4-tetrahydroisoquinoline;
1-[1-(cyclohex-1-en-3-yl)cyclobutyl]-7-hydroxy-2,6-dimethyl-1,2,3,4-tetrahydroisoquinoline;
7-hydroxy-2,6-dimethyl-1-[1-(1,2,3,4-tetrahydronaphth-1-yl)cyclopropyl]-1,2,3,4-tetrahydroisoquinoline;
7-hydroxy-2,6-dimethyl-1-[1-(2-thienyl)cyclopropyl]-1,2,3,4-tetrahydroisoquinoline;
7-hydroxy-2,6-dimethyl-1-[1-(3-thienyl)cyclopropyl]-1,2,3,4-tetrahydroisoquinoline;
1-[1-(2-furyl)cyclopropyl]-7-hydroxy-2,6-dimethyl-1,2,3,4-tetrahydroisoquinoline;
7-hydroxy-2-methyl-1-[1-(2-pyridyl)cyclobutyl]-1,2,3,4-tetrahydroisoquinoline;
7-hydroxy-2,6-dimethyl-1-[1-(2-pyridyl)cyclopropyl]-1,2,3,4-tetrahydroisoquinoline;
and pharmaceutically acceptable salts thereof in the form of individual enantiomers, racemates or other mixtures of enantiomers.

10. Tetrahydroisoquinoline compounds of formula II

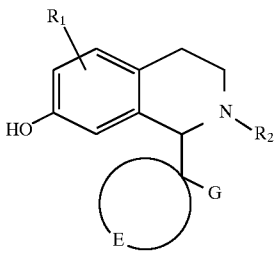

and pharmaceutically acceptable salts thereof in the form of individual enantiomers, racemates, or other mixtures of enantiomers, in which $R_1$, $R_2$, E and G are as defined in claim 1 and O-acylated derivatives thereof.

11. Tetrahydroisoquinoline compounds of formula III

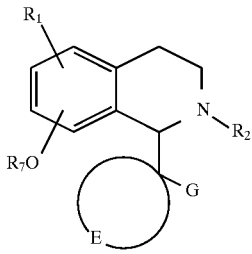

and pharmaceutically acceptable salts thereof in the form of individual enantiomers, racemates, or other mixtures of enantiomers, in which $R_1$, $R_2$, E and G are as defined in claim 1 and $R_7$ represents an acyl group derived from a carboxylic acid having 6 to 20 carbon atoms, preferably 7 to 18 carbon atoms.

12. Pharmaceutical compositions comprising a therapeutically effective amount of a compound of formula I, as defined in claim 1 together with a pharmaceutically acceptable diluent or carrier.

13. A method of inducing analgesia or of treating psychoses, Parkinson's disease, Lesch-Nyan syndrome, attention deficit disorder or cognitive impairment or in the relief of drug dependence or tardive dyskinesia which comprises the administration of a therapeutically effective amount of a compound of formula I as claimed in claim 1 to a patient in need thereof.

14. A method as claimed in claim 13 for treating schizophrenia.

15. A process for the preparation of compounds of formula I as defined in claim 1:

a) by the cleavage of compounds of formula IV

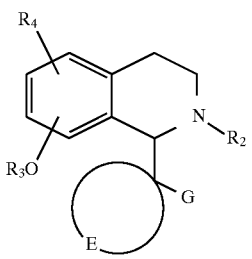

in which $R_3$ is an optionally substituted alkyl group and $R_4$ is the group $R_1$ or a group which can be converted into the group $R_1$; or b) by the alkylation or alkenylation of compounds of formula V

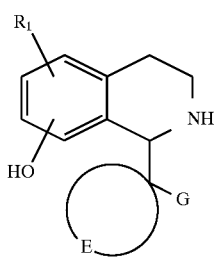

V under conditions which do not result in alkylation or alkenylation of the hydroxy group.

16. The compound of formula III, as defined in claim 11, wherein $R_7$ represents heptanoyl, decanoyl, dodecanoyl, hexadecanoyl or octadecanoyl.

17. The compound of formula III, as defined in claim 11, wherein the group $OR_7$ is in the 7-position.

18. A method of inducing analgesia or of treating psychoses, Parkinson's disease, Lesch-Nyan syndrome, attention deficit disorder or cognitive impairment or in the relief of drug dependence or tardive dyskinesia which method comprises administering a therapeutically effective amount of a compound of formula II, as defined in claim 10, to a patient in need thereof.

19. A method of inducing analgesia or of treating psychoses, Parkinson's disease, Lesch-Nyan syndrome, attention deficit disorder or cognitive impairment or in the relief of drug dependence or tardive dyskinesia which method comprises administering a therapeutically effective amount of a compound of formula III, as defined in claim 11, to a patient in need thereof.

* * * * *

UNITED STATES PATENT AND TRADEMARK OFFICE
CERTIFICATE OF CORRECTION

PATENT NO. : 5,807,868

DATED : September 15, 1998

INVENTOR(S) : SARGENT et al.

It is certified that error appears in the above-identified patent and that said Letters Patent is hereby corrected as shown below:

Col. 31, claim 7, lines 12 to 26, delete the following material:

" (a) a saturated or unsaturated alicyclic group containing 5 to 7 carbon atoms optionally substituted by one or more substitutents selected from alkyl of 1 to 3 carbon atoms, hydroxy, alkoxy of 1 to 3 carbon atoms, polyfluoroalkyl of 1 to 3 carbon atoms, oxo, alkylthio of 1 to 3 carbon atoms, alkylsulphinyl of 1 to 3 carbon atoms or alkylsulphonyl of 1 to 3 carbon atoms, said alicyclic group being optionally fused to one or more further rings to form a polycyclic group or (b) a saturated or unsaturated aliphatic chain containing 1 to 10 carbon atoms optionally substituted by one or more substituents selected from alkyl of 1 to 3 carbon atoms, hydroxy, alkoxy of 1 to 3 carbon atoms, polyfluoroalkyl of 1 to 3 carbon atoms, cycloalkyl of 3 to 7 carbon atoms, oxo, alkylthio of 1 to 3 carbon atoms, alkylsulphinyl of 1 to 3 carbon atoms or alkylsulphonyl of 1 to 3 carbon atoms, or (c) "

Col. 31, claim 8, lines 42 and 43, delete "methylalkyl, cycloalkylmethyl, cycloalkenyl, 1,2,3,4-tetrahydronaphthyl,".

UNITED STATES PATENT AND TRADEMARK OFFICE
CERTIFICATE OF CORRECTION

PATENT NO. : 5,807,868
DATED : September 15, 1998
INVENTOR(S) : Sargent et al.

It is certified that error appears in the above-identified patent and that said Letters Patent is hereby corrected as shown below:

Col. 31, claim 9, lines 47 to 54, delete the following material:

" 7-hydroxy-2-methyl-1-[1-(2-methylpropyl)cyclobutyl]-1,2,3,4-tetrahydroisoquinoline;

1-[1-(cyclopentylmethyl)cyclopropyl]-7-hydroxy-2,6-dimethyl-1,2,3,4-tetrahydroisoquinoline;

1-[1-(cyclohex-1-en-3-yl)cyclobutyl]-7-hydroxy-2,6-dimethyl-1,2,3,4-tetrahydroisoquinoline;

7-hydroxy-2,6-dimethyl-1-[1-(1,2,3,4-tetrahydronaphth-1-yl)cyclopropyl]-1,2,3,4-tetrahydroisoquinoline; "

Signed and Sealed this

Thirteenth Day of July, 1999

Attest:

Q. TODD DICKINSON

*Attesting Officer*  *Acting Commissioner of Patents and Trademarks*